United States Patent
Pamer et al.

(10) Patent No.: US 11,197,897 B2
(45) Date of Patent: Dec. 14, 2021

(54) METHODS AND COMPOSITIONS FOR REDUCING VANCOMYCIN-RESISTANT ENTEROCOCCI INFECTION OR COLONIZATION

(71) Applicant: Memorial Sloan Kettering Cancer Center, New York, NY (US)

(72) Inventors: Eric Pamer, Montclair, NJ (US); Peter McKenney, New York, NY (US); Silvia Caballero, Cambridge, MA (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/870,634

(22) Filed: May 8, 2020

(65) Prior Publication Data
US 2021/0000887 A1    Jan. 7, 2021

Related U.S. Application Data

(62) Division of application No. 15/986,369, filed as application No. PCT/US2016/063643 on Nov. 23, 2016, now Pat. No. 10,646,520.

(60) Provisional application No. 62/260,164, filed on Nov. 25, 2015, provisional application No. 62/301,873, filed on Mar. 1, 2016.

(51) Int. Cl.
| | |
|---|---|
| *A61K 39/00* | (2006.01) |
| *A61K 39/08* | (2006.01) |
| *A61K 39/09* | (2006.01) |
| *A61K 35/741* | (2015.01) |
| *A61K 35/74* | (2015.01) |
| *C12N 1/20* | (2006.01) |
| *A61P 31/04* | (2006.01) |
| *A61K 9/00* | (2006.01) |

(52) U.S. Cl.
CPC .......... *A61K 35/741* (2013.01); *A61K 9/0031* (2013.01); *A61K 9/0043* (2013.01); *A61K 9/0053* (2013.01); *A61K 35/74* (2013.01); *A61P 31/04* (2018.01); *C12N 1/20* (2013.01); *C12Y 101/00* (2013.01); *C12Y 101/01201* (2013.01)

(58) Field of Classification Search
CPC ........ A61K 39/00; A61K 39/02; A61K 39/08; A61K 39/09
USPC ...................... 424/234.1, 239.1, 246.1, 247.1
See application file for complete search history.

(56) References Cited

U.S. PATENT DOCUMENTS 8,460,648 B2    6/2013    Borody

FOREIGN PATENT DOCUMENTS

| WO | WO 94/08598 A1 | 4/1994 |
| WO | WO 2014/082050 A1 | 5/2014 |
| WO | WO 2014/177667 A1 | 11/2014 |
| WO | WO 2015/077794 A1 | 5/2015 |

OTHER PUBLICATIONS

U.S. Appl. No. 15/986,369 (U.S. Pat. No. 10,646,520), filed May 22, 2018 (May 12, 2020).
U.S. Appl. No. 15/986,369, dated Apr. 6, 2020 Issue Fee Payment.
U.S. Appl. No. 15/986,369, dated Jan. 13, 2020 Notice of Allowance.
U.S. Appl. No. 15/986,369, dated Dec. 20, 2019 Response to Final Office Action.
U.S. Appl. No. 15/986,369, dated Sep. 20, 2019 Final Office Action.
U.S. Appl. No. 15/986,369, dated Jun. 20, 2019 Response to Non-Final Office Action.
U.S. Appl. No. 15/986,369, dated Dec. 21, 2018 Non-Final Office Action.
U.S. Appl. No. 15/986,369, dated Dec. 3, 2018 Response to Restriction Requirement.
U.S. Appl. No. 15/986,369, dated Oct. 2, 2018 Restriction Requirement.
U.S. Appl. No. 15/986,369, dated Jun. 27, 2018 Preliminary Amendment.
Atta, "Gene therapy for liver regeneration: Experimental studies and prospects for clinical trials," World J Gastroenterol., 16(32):4019-4030 (2010).
Begley et al., "Bile Salt Hydrolase Activity in Probiotics," Appl. Environ Microbiol. 72(3):1729-1738 (2006).
Buffie et al., "Microbiota-mediated colonization resistance against intestinal pathogens," Nature Reviews Immunology 13:790-801 (2013).
Caballero et al., "Distinct but Spatially Overlapping Intestinal Niches for Vancomycin-Resistant Enterococcus faecium and Carbapenem-Resistant Klebsiella neumoniae," PLOS Pathogens (PRINT), 11(9):e1005132 (2015).
Cline, "Perspectives for Gene Therapy: Inserting New Genetic Information into Mammalian Cells by Physical Techniques and Viral Vectors," Pharmac. Ther. 29:69-92 (1985).
Cotten et al., "Receptor-Mediated Transport of DNA into Eukaryotic Cells," Meth Enzymol. 217:618-644 (1993).

(Continued)

*Primary Examiner* — Rodney P Swartz
(74) *Attorney, Agent, or Firm* — Baker Botts L.L.P.

(57) ABSTRACT

The present invention relates to methods and compositions for reducing the risk and severity of vancomycin-resistant *Enterococci* infection or colonization. It is based, at least in part, on the discovery that a restricted fraction of the gut microbiota, including the bacteria *Clostridium scindens* and/ or the bacteria *Blautia producta* contribute substantially to resistance against vancomycin-resistant *Enterococci* infection or colonization. Without being bound by any particular theory, it is believed that this is achieved through the biosynthesis of secondary bile acids in the case of *Clostridium scindens*.

Figure 1:
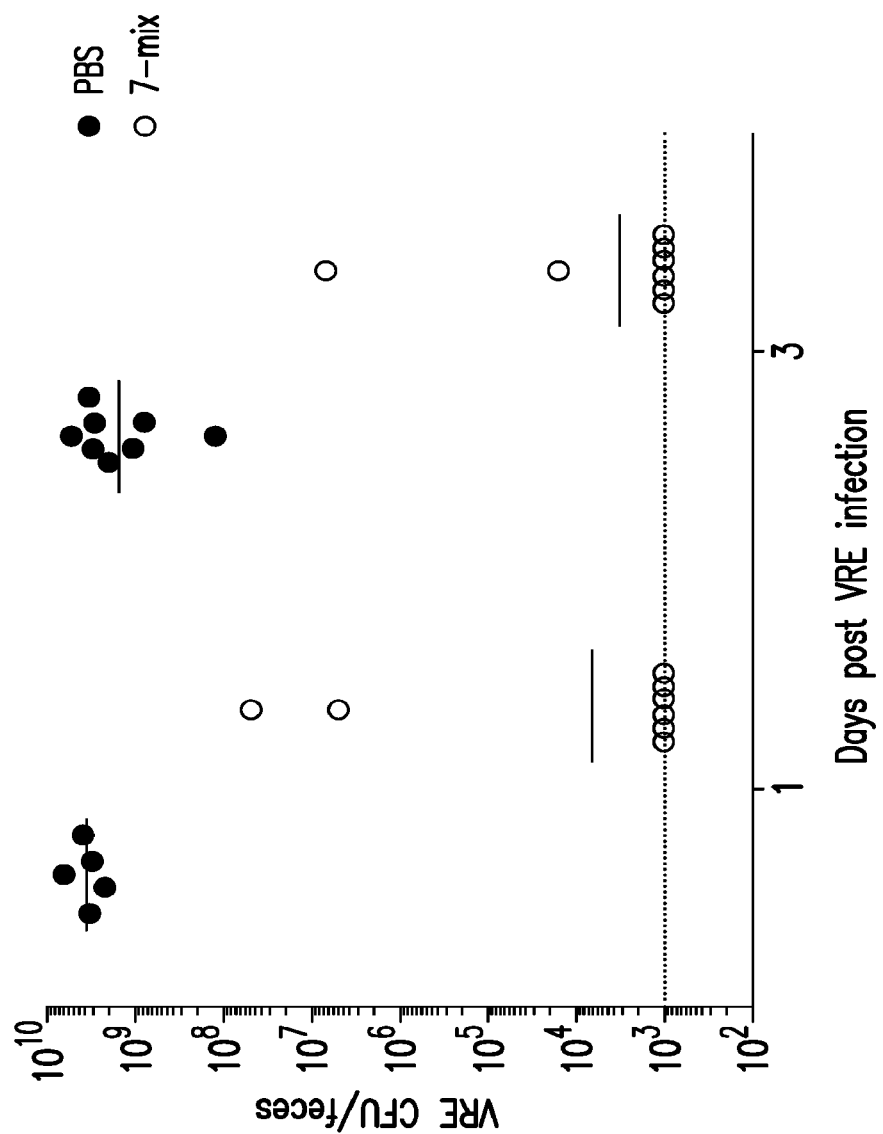

21 Claims, 10 Drawing Sheets
Specification includes a Sequence Listing.

(56) References Cited

OTHER PUBLICATIONS

Extended European Search Report dated Jul. 26, 2019 in EP Application No. 16869296.
Ezaki et al. "16S Ribosomal DNA Sequences of Anaerobic Cocci and Proposal of *Ruminococcus hansenii* comb. nov. and *Ruminococcus productus* comb. nov.," Int J Syst Bacteriol. 44(1):130-136 (1994).
Goldspiel et al., "Human Gene Therapy," Clinical Pharmacy 12:488-505 (1993).
International Search Report dated Mar. 9, 2017 in International Application No. PCT/US2016/063643.
Krafft et al., "Purification and Characterization of a Novel Form of 20α-Hydroxysteroid Dehydrogenase from Clostridium scindens," J Bacteriol., 171(6):2925-2932 (1989).
Kriegler, Gene Transfer and Expression, A Laboratory Manual, Stockton Press, NY (1990).
Kron et al., "Adenovirus Vectors and Subviral Particles for Protein and Peptide Delivery," Curr Gene Ther 12:362-373 (2012).
Liu et al., "Reclassification of Clostridium coccoides, Ruminococcus hansenii Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces.," Int. J. Syst. Evol. Microbiol., 58:1896-1902 (2008).
Loeffler et al., "Gene Transfer into Primary and Established Mammalian Cell Lines with Lipopolyamine-Coated DNA," Meth Enzymol., 217:599-618 (1993).
McAuliffe et al., "Genetic Analysis of Two Bile Salt Hydrolase Activities in Lactobacillus acidophilus NCFM," Appl. Environ Microbiol., 71(8):4925-4929 (2005).
Morgan et al., "Human Gene Therapy," Ann. Rev. Biochem., 62:191-217 (1993).
Morris et al., "*Clostridium scindens* sp. nov., a Human Intestinal Bacterium with Desmolytic Activity on Corticoids," Int J Syst. Bacteriol., 35(4):478-481 (1985).
Mulligan, "The Basic Science of Gene Therapy," Science 260(5110):926-932 (1993).
Pittelkow et al., "New Techniques for the In Vitro Culture of Human Skin Keratinocytes and Perspectives on Their Use for Grafting of Patients with Extensive Burns," Mayo Clinic Proc. 61:771-777 (1986).
Porada et al., "Treatment of Hemophilia A in Utero and Postnatally using Sheep as a Model for Cell and Gene Delivery," J. Genet Syndr Gene Ther., 25:Suppl. 1, 26 pages (2012).
Remington's Pharmaceutical Sciences, 18th ed. A. R. Gennaro, ed. Mack, Easton, PA (1990) (Table of Contents).
Rheinwald, "Chapter 15: Serial Cultivation of Normal Human Epidermal Keratinocytes," Meth. Cell Biology, 21A:229-254 (1980).
Ridlon et al., "Bile salt biotransformations by human intestinal bacteria," J Lipid Res 47:241-259 (2006).
Ridlon et al., "Clostridium scindens: a human gut microbe with a high potential to convert glucocorticoids into androgens," J. Lipid Res. 54:2437-2449 (2013).
Ridlon et al., "Identification and characterization of two bile acid coenzyme A transferases from Clostridium scindens, a bile acid 7a-dehydroxylating intestinal bacterium," J. Lipid Res. 53:66-76 (2012).
Stemple et al., "Isolation of a Stem Cell for Neurons and Glia from the Mammalian Neural Crest," Cell 71:973-985 (1992).
Tolstoshev, "Gene Therapy, Concepts, Current Trials and Future Directions," Ann. Rev. Pharmacol. Toxicol. 32:573-596 (1993).
Trends in Biotechnology, TIBTECH 11 (5): 155-215 (1993) (Table of Contents).
Ubeda et al., "Intestinal Microbiota Containing *Barnesiella* Species Cures Vancomycin-Resistant Enterococcus Faecium Colonization," Infection and Immunity, 81(3):965-973 (2013).
Ubeda et al., "Vancomycin-resistant *Enterococcus* domination of intestinal microbiota is enabled by antibiotic treatment in mice and precedes bloodstream invasion in humans," The Journal of Clinical Investigation, 120:4332-4341 (2010).
Wu et al., "Delivery systems for gene therapy," Biotherapy 3:87-95 (1991).
Yi et al., "Current Advances in Retroviral Gene Therapy," Curr Gene Ther 11:218-228 (2011).

SEQUENCE LISTING

```
<160> NUMBER OF SEQ ID NOS: 4

<210> SEQ ID NO 1
<211> LENGTH: 266
<212> TYPE: PRT
<213> ORGANISM: Clostridium scindens

<400> SEQUENCE: 1

Met Arg Leu Lys Asp Lys Val Ile Leu Val Thr Ala Ser Thr Arg Gly
1               5                   10                  15

Ile Gly Leu Ala Ile Ala Gln Ala Cys Ala Lys Glu Gly Ala Lys Val
            20                  25                  30

Tyr Met Gly Ala Arg Asn Leu Glu Arg Ala Lys Ala Arg Ala Asp Glu
        35                  40                  45

Met Asn Ala Ala Gly Gly Asn Val Lys Tyr Val Tyr Asn Asp Ala Thr
    50                  55                  60

Lys Glu Glu Thr Tyr Val Thr Met Ile Glu Glu Ile Ile Glu Gln Glu
65                  70                  75                  80

Gly Arg Ile Asp Val Leu Val Asn Asn Phe Gly Ser Ser Asn Pro Lys
                85                  90                  95

Lys Asp Leu Gly Ile Ala Asn Thr Asp Pro Glu Val Phe Ile Lys Thr
            100                 105                 110

Val Asn Ile Asn Leu Lys Ser Val Phe Ile Ala Ser Gln Thr Ala Val
        115                 120                 125

Lys Tyr Met Ala Glu Asn Gly Gly Ser Ile Ile Asn Ile Ser Ser
    130                 135                 140

Val Gly Gly Leu Ile Pro Asp Ile Ser Gln Ile Ala Tyr Gly Thr Ser
145                 150                 155                 160

Lys Ala Ala Ile Asn Tyr Leu Thr Lys Leu Ile Ala Val His Glu Ala
                165                 170                 175

Arg His Asn Ile Arg Cys Asn Ala Val Leu Pro Gly Met Thr Ala Thr
            180                 185                 190

Asp Ala Val Gln Asp Asn Leu Thr Asp Asp Phe Arg Asn Phe Phe Leu
        195                 200                 205

Lys His Thr Pro Ile Gln Arg Met Gly Leu Pro Glu Glu Ile Ala Ala
    210                 215                 220

Ala Val Val Tyr Phe Ala Ser Asp Asp Ala Ala Tyr Thr Thr Gly Gln
225                 230                 235                 240

Ile Leu Thr Val Ser Gly Gly Phe Gly Leu Ala Thr Pro Ile Phe Gly
                245                 250                 255
```

Asp Leu Ser Glu Arg Ser Asp Ala Arg Gly
       260               265

<210> SEQ ID NO 2
<211> LENGTH: 1305
<212> TYPE: DNA
<213> ORGANISM: Clostridium scindens

<400> SEQUENCE: 2

```
ggccggaatg cagaagttgt ccctggcgtt tttatgaagg cgaccggcat gagatattga    60
acgagacaga ccgggaacag gtatatgaag acctgttcca atggattgaa gatcagaaaa   120
tgacgcagca aaattaggac gctatactta agaaaagtat ccggataatg attacatgaa   180
tatgaaagat atctggaata ctaaaaataa atcatatgga gggattacac atgaggttaa   240
aagacaaagt gattctggtt acagcatcca ccagaggcat tggcctggct atcgctcagg   300
catgtgcgaa agaaggagcc aaagtctaca tgggcgccag gaatctggaa cgcgccaagg   360
cacgggctga cgagatgaat gcggcaggcg gcaatgtaaa gtatgtttac aatgatgcga   420
caaaagaaga gacatacgtg acgatgattg aggaaatcat cgagcaagaa gggcgcatag   480
acgtgcttgt aaataatttc ggctcatcaa atcccaagaa agatcttgga attgccaata   540
cagacccgga ggtattcatc aagacggtaa atatcaacct aaagagcgta tttatcgcaa   600
gccagacggc tgttaagtat atggcggaaa atggaggtgg aagcatcatc aatatctcat   660
ccgtaggagg cctgatacca gatatctctc agattgccta tggaaccagc aaagcggcaa   720
tcaactatct gacgaaactg atagccgtac acgaggcaag gcataacatc agatgcaatg   780
cggtacttcc aggaatgacg gcaacagatg cggtgcagga taatctgacg gatgacttcc   840
gaaacttctt cttgaagcat acgccaattc agcgtatggg gctcccggaa gagatcgcgg   900
cagccgtagt atacttcgca agcgatgatg ccgcatatac cacaggacag attcttaccg   960
tatctggcgg tttcggactg gcaacgccga tatttggaga tctgtctgaa cgctcagatg  1020
cccgcgggta gaatttcatg ggttaactta atcaaaagca gaatcaggaa aagagacagc  1080
cgggagcggc tgtctctttt atctatagtc gcctagcgg cgcacgtttc taactttata  1140
ggaaagttct cctttcggag aacttgggga ctaaaatagc ccgctcaaaa gcgggcatag  1200
tgaatcagac ggtttggatt aaaagatgta aaagccctct tcaccaaaat cgtcatcatc  1260
aaggttatca aattcatgta agaaataatc catatccaga agttc             1305
```

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
     primer
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other

<400> SEQUENCE: 3
nnnnnnnnnn nnnnnnnnnn aytgggydta aagng    35

<210> SEQ ID NO 4
<211> LENGTH: 38

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(20)
<223> OTHER INFORMATION: a, c, t, g, unknown or other

<400> SEQUENCE: 4
nnnnnnnnnn nnnnnnnnnn ccgtcaatty htttragt                            38
```

METHODS AND COMPOSITIONS FOR REDUCING VANCOMYCIN-RESISTANT ENTEROCOCCI INFECTION OR COLONIZATION

CROSS-REFERENCE TO RELATED APPLICATIONS

The present application is a divisional of U.S. patent application Ser. No. 15/986,369, filed May 22, 2018, now U.S. Pat. No. 10,646,520, which is a continuation of International Application No. PCT/US2016/063643, filed Nov. 23, 2016, which claims priority to U.S. Provisional Application Ser. No. 62/260,164, filed Nov. 25, 2015, and U.S. Provisional Application Ser. No. 62/301,873, filed Mar. 1, 2016, both titled METHODS AND COMPOSITIONS COMPRISING PROBIOTICS FOR REDUCING VANCOMYCIN-RESISTANT ENTEROCOCCI INFECTION, the contents of each of which are incorporated by reference herein in their entirety, and to each of which priority is claimed.

STATEMENT OF GOVERNMENT INTEREST

This invention was made with government support under AI042135, CA009149 and CA008748 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on May 8, 2020, is named 072734_1035_SL.txt and is 5,265 bytes in size.

1. INTRODUCTION

The present invention relates to compositions and methods for decreasing the risk of developing vancomycin-resistant *Enterococci* (VRE) infection or colonization and for treating VRE infection or colonization.

2. BACKGROUND OF THE INVENTION

The gastrointestinal tract of mammals is densely colonized by hundreds of microbial species that coexist symbiotically with their hosts. The microbes, collectively referred to as the microbiota, contribute to numerous aspects of host health, including nutrient metabolism, homeostasis of intestinal tissues, development of innate and adaptive immune responses, and more generally, defense against intestinal infection. Bacteria antagonize intestinal pathogens directly, through contact-dependent and soluble factor-mediated inhibition, as well as indirectly by calibrating and inducing host immune responses, but the contributions of individual bacteria to colonization resistance against specific pathogens are not well understood.

*Enterococci* are a genus of gram-positive, round-shaped bacteria that commonly live in the gut, although they can cause infection anywhere in the body. The genus has a high amount of intrinsic resistance to some classes of antibiotics, but is generally sensitive to vancomycin. However, particularly virulent strains that are resistant even to vancomycin are an emerging and are a growing problem, particularly in institutional settings. Such vancomycin-resistant strains are referred to as VRE. The two main VRE species are vancomycin-resistant *Enterococcus faecium* (*E. faecium*) and vancomycin-resistant *Enterococcus faecalis* (*E. faecalis*). VRE can exist in the body, typically in the gastrointestinal tract, without causing a disease or other harmful effects. However, VRE can sometimes cause local disease in the gastrointestinal tract and they can invade sites outside the gastrointestinal tract and cause disease, for example, in the bloodstream, abdomen, or urinary tract. VRE in the bloodstream can be particularly problematic because, once in the bloodstream, VRE can cause sepsis, meningitis, pneumonia, or endocarditis.

3. SUMMARY OF THE INVENTION

According to a first embodiment, the invention provides for a method for reducing the risk of VRE infection or VRE colonization in a subject, and/or increasing resistance to VRE infection or VRE colonization in the subject, and/or reducing the severity of VRE infection in the subject, and/or reducing the amount of VRE colonizing the subject, comprising administering, to the subject in need of such treatment, a therapeutically effective amount of a composition comprising at least one of a *Clostridium scindens* (*C. scindens*) bacteria and/or a *Blautia producta* (*B. producta*) bacteria in a formulation suitable for administration to the subject.

According to additional embodiments, which may be combined with the first embodiment and with one another, unless clearly mutually exclusive, the invention provides:

the composition comprises both the *C. scindens* bacteria and the *B. producta* bacteria;

the composition further comprises one or more additional species of bacteria selected from the group consisting of a member of the Bacteroidetes phylum and a member of the Firmicutes phylum, such as a member of the Lachnospiraceae family;

the composition further comprises one or more additional species of bacteria selected from the group consisting of a *Barnesiella intestihominis* (*B. intestihominis*), *Blautia hansenii* (*B. hansenii*), *Pseudoflavonifractor capillosus* (*P. capillosus*), *Clostridium hiranonis* (*C. hiranonis*), *Clostridium hylemonae* (*C. hylemonae*), *Clostridium perfringens* (*C. perfringens*), *Clostridium sordellii* (*C. sordellii*), *Proteocatella sphenisci* (*P. sphenisci*) Lachnospiraceae 5_1_57FAA, Clostridiales VE202-05 and Clostridiales VE202-26;

the composition further comprises the *C. scindens* bacteria and a *B. hansenii* bacteria;

the composition further comprises the *B. producta* bacteria and a *Clostridium bolteae* (*C. bolteae*) bacteria;

the composition further comprises one or more additional species of bacteria selected from the group consisting of *Parabacteroides distasonis* (*P. distasonis*), *Bacteroides sartorii* (*B. sartorii*), *Clostridium innocuum* (*C. innocuum*), *Akkermansia muciniphila* (*A. muciniphila*), *C. bolteae*, *Blautia unclassified*, and *Eubacterium dolichum* (*E. dolichum*);

the one or more recombinant bacteria can express one or more of a recombinant enzyme that can convert a primary bile acid to a secondary bile acid, synthesize a recombinant antibiotic resistance molecule, express a recombinant protease, and express a recombinant glycosidase;

the recombinant enzyme that can convert a primary bile acid to a secondary bile acid is a bile acid hydroxysterol dehydrogenase enzyme;

the method comprises administering at least one bacteria as an isolated viable bacteria;

the method comprises administering at least one bacteria as an isolated spore thereof;

the composition is formulated for oral, nasogastric, or rectal administration;

the composition further comprises a probiotic bacteria, probiotic yeast, or a combination thereof;

the composition is a liquid, suspension, dried powder, tablet, capsule or food product;

the method further comprises administering to the subject, an antibiotic, an immunotherapeutic agent, an herbal remedy, a probiotic bacteria, a probiotic yeast, or a combination thereof;

the therapeutically effective amount ameliorates at least one symptom of VRE infection selected from the group consisting of abdominal tenderness, abdominal pain, abdominal cramping, sepsis, endocarditis, meningitis, headache, stiff neck, confusion, back pain, pneumonia, fever, chills, diarrhea, urinary tract infection, endocarditis, elevated white blood cell count, and decreased serum albumin;

the therapeutically effective amount inhibits proliferation of VRE in the gastrointestinal tract of the subject;

the method further comprises evaluating the VRE infection or VRE colonization in the subject by culturing a sample from the subject; and the method further comprises evaluating the VRE infection or VRE colonization in the subject by detecting a VRE biomarker in a sample from the subject.

According to a second embodiment, the invention provides a therapeutic composition for treating VRE infection, the composition comprising at least one of an isolated *C. scindens* bacteria or an isolated *B. producta* bacteria in a formulation suitable for administration to a subject.

According to additional embodiments, which may be combined with the second embodiment and with one another, unless clearly mutually exclusive, the invention provides:

the composition comprising both the *C. scindens* therapeutic bacteria and the *B. producta* therapeutic bacteria;

the composition further comprising one or more additional species of bacteria selected from the group consisting of a member of the Bacteroidetes phylum and a member of the Firmicutes phylum, such as a member of the Lachnospiraceae family;

the composition further comprising one or more additional species of bacteria selected from the group consisting of a *B. intestihominis, B. hansenii, P. capillosus, C. hiranonis, C. hylemonae, C. perfringens, C. sordellii, P. sphenisci*, Lachnospiraceae 5_1_57FAA, Clostridiales VE202-05 and Clostridiales VE202-26;

the composition further comprising the *C. scindens* bacteria and a *B. hansenii* bacteria;

the composition further comprising the *B. producta* bacteria and *C. bolteae* bacteria;

the composition further comprising one or more additional species of bacteria selected from the group consisting of *P. distasonis, B. sartorii, C. innocuum, A. muciniphila, C. bolteae*, Blautia unclassified, and *E. dolichum*;

the composition wherein bacteria of the composition can express an enzyme that can convert a primary bile acid to a secondary bile acid, synthesize an antibiotic resistance molecule, express a protease, and express a glycosidase;

the composition wherein the one or more recombinant bacteria can express one or more of a recombinant enzyme that can convert a primary bile acid to a secondary bile acid, synthesize a recombinant antibiotic resistance molecule, express a recombinant protease, and express a recombinant glycosidase;

the composition wherein the recombinant enzyme that converts a primary bile acid to a secondary bile acid is a bile acid hydroxysterol dehydrogenase enzyme;

the composition wherein at least one isolated bacteria is an isolated spore thereof;

the composition wherein the composition is formulated for oral, nasogastric, or rectal administration;

the composition further comprising a probiotic bacteria, probiotic yeast, or a combination thereof;

the composition as a liquid, suspension, dried powder, tablet, capsule or food product.

The above methods may be used employing any of the above compositions.

In a third embodiment, the present invention provides for the use of any of the above compositions for treatment of VRE infection or VRE colonization in a subject. The use may include administering to the subject a therapeutically effective amount of the composition. The use may further include actions described in connection with any of the method described above.

4. BRIEF DESCRIPTION OF THE FIGURES

For a more complete understanding of the present invention and its features and advantages, reference is now made to the following description, taken in conjunction with the accompanying drawings, which are not to scale, in which like numerals refer to like features, and in which:

FIG. 1 is a graph of VRE colony forming units (CFU) in mice feces versus days post infection in the presence of antibiotics for mice treated with a bacterial suspension of *P. distasonis, B. sartorii* (also known as *Bacteroides chinchillae*), *B. producta, C. innocuum, A. muciniphila, C. bolteae*, and *Blautia* unclassified (7-mix) or with phosphate buffered saline (PBS).

Figure 2A:
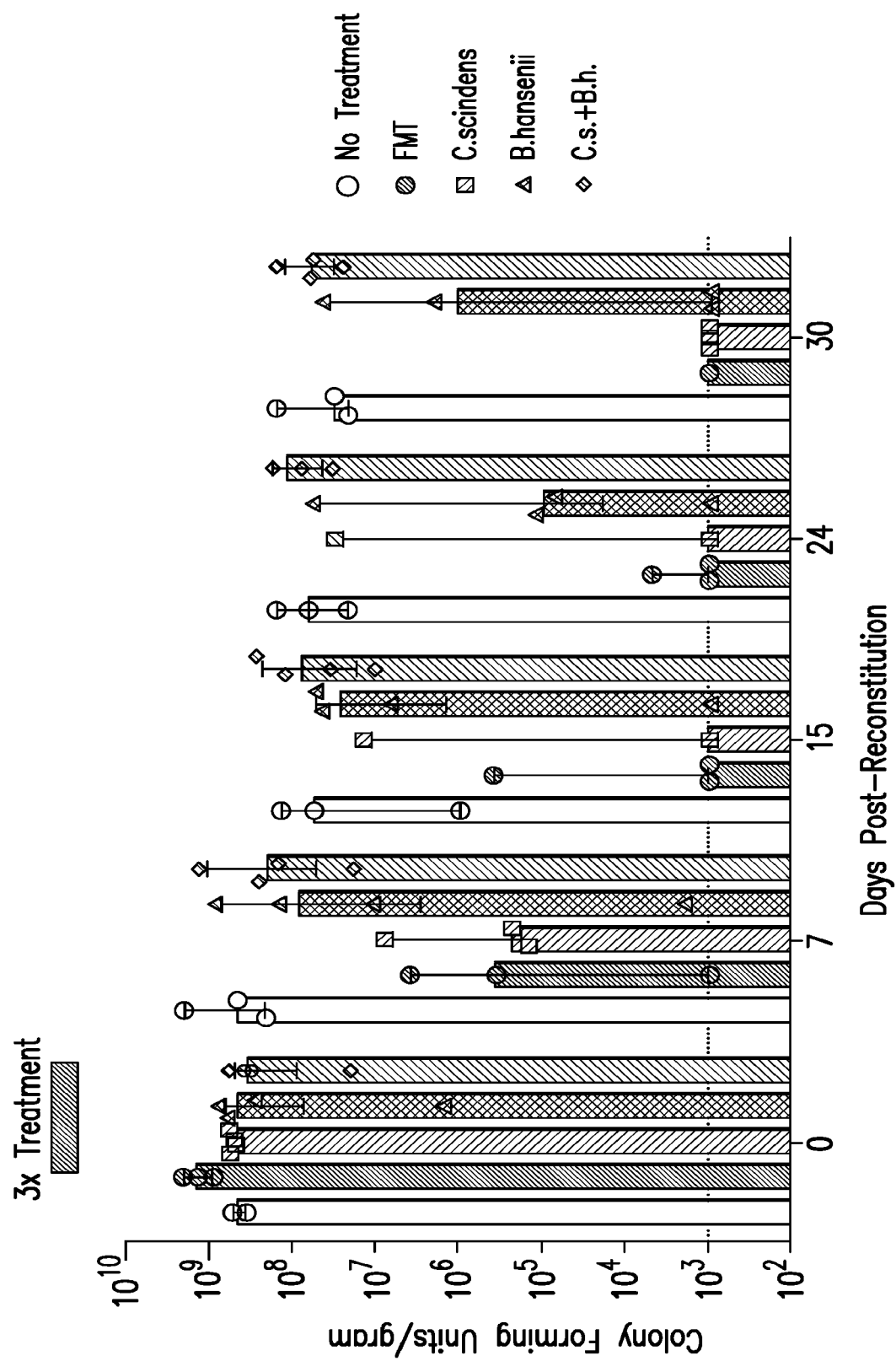
Figure 2B:
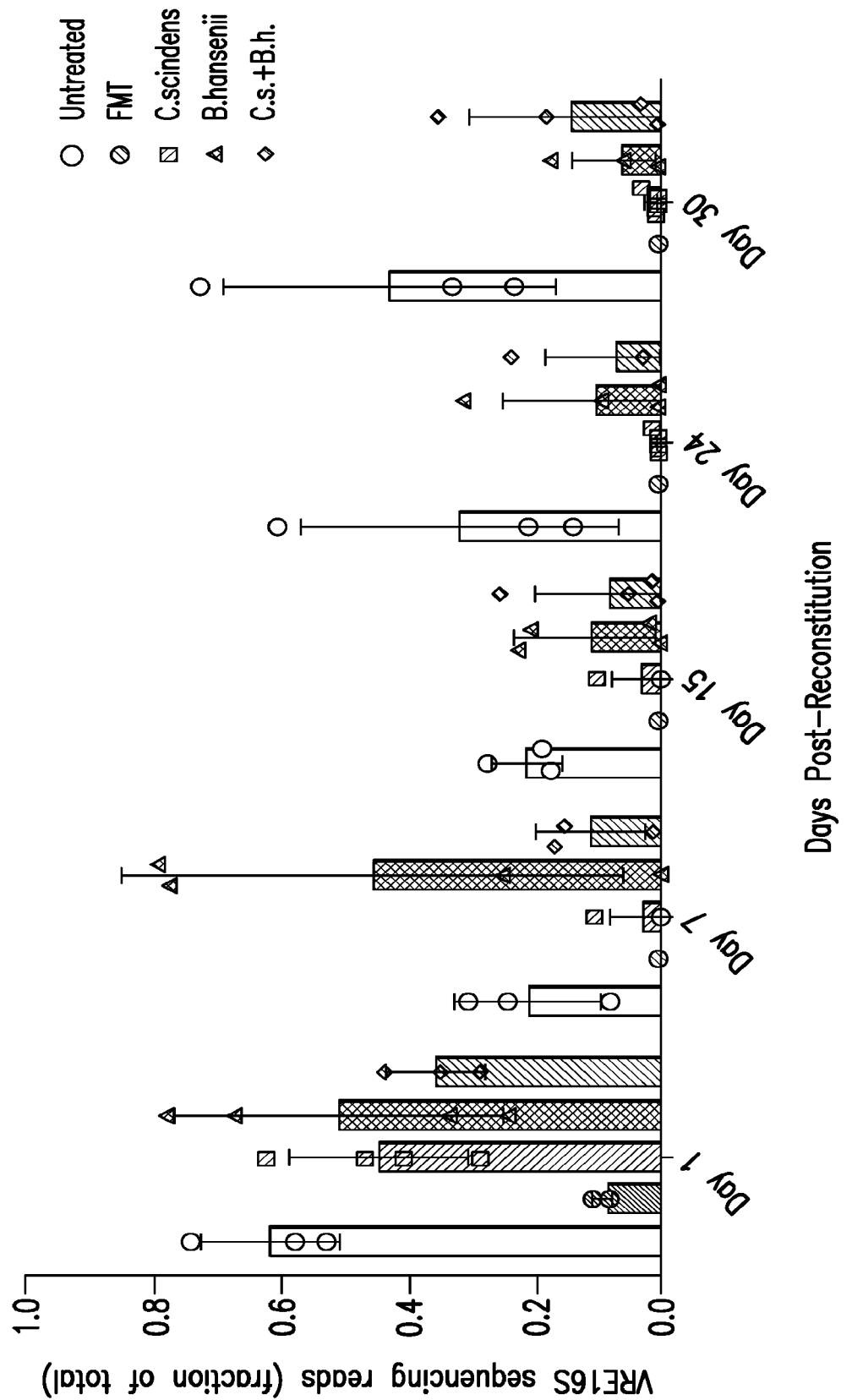
Figure 2C:
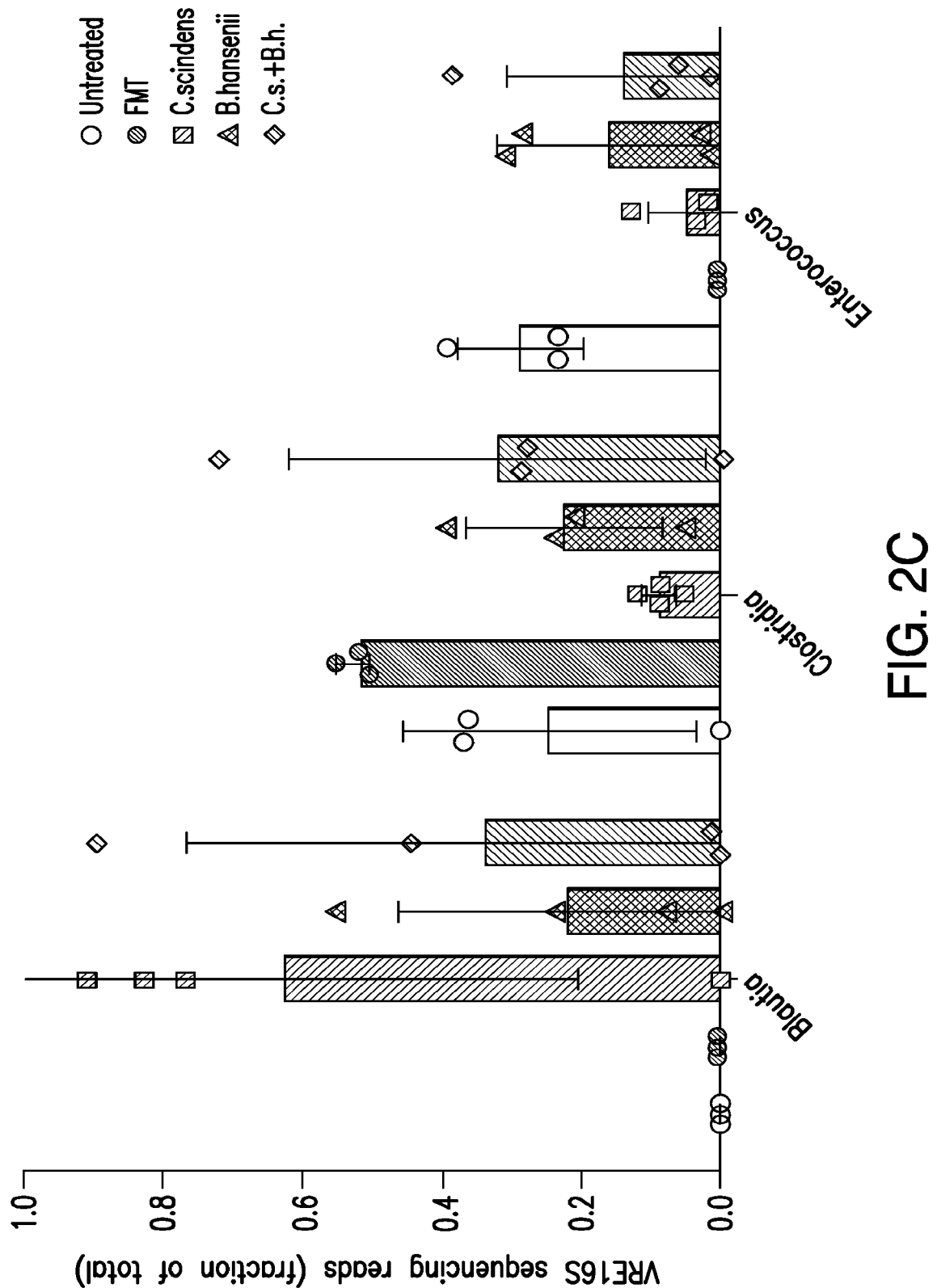

FIGS. 2A-2C show the effect of *C. scindens* and *B. hansenii* on VRE intestinal clearance in mice in vivo over a 30 day study period. Mice infected with VRE and then treated with a Fecal Microbiota Transplant (FMT) (n=3), *C. scindens* (n=4), *B. hansenii* (n=4), or a mixture of *C. scindens* and *B. hansenii* (C.s.+B.h) (n=4). Control mice (No treatment) (n=4) were untreated. In FIGS. 2A-2C, bars represent the median, whiskers represent inter-quartile range.

FIG. 2A is a graph of VRE CFU in mice feces over the study period. FIG. 2B is graph of amount of VRE spp. 16S sequence reads over the study period. FIG. 2C is a graph of the amount of *Blautia* spp. 16S sequence reads, *Clostridium* spp. 16S sequence reads, and VRE spp. 16S sequence reads at day 15 post-reconstitution.

Figure 3:
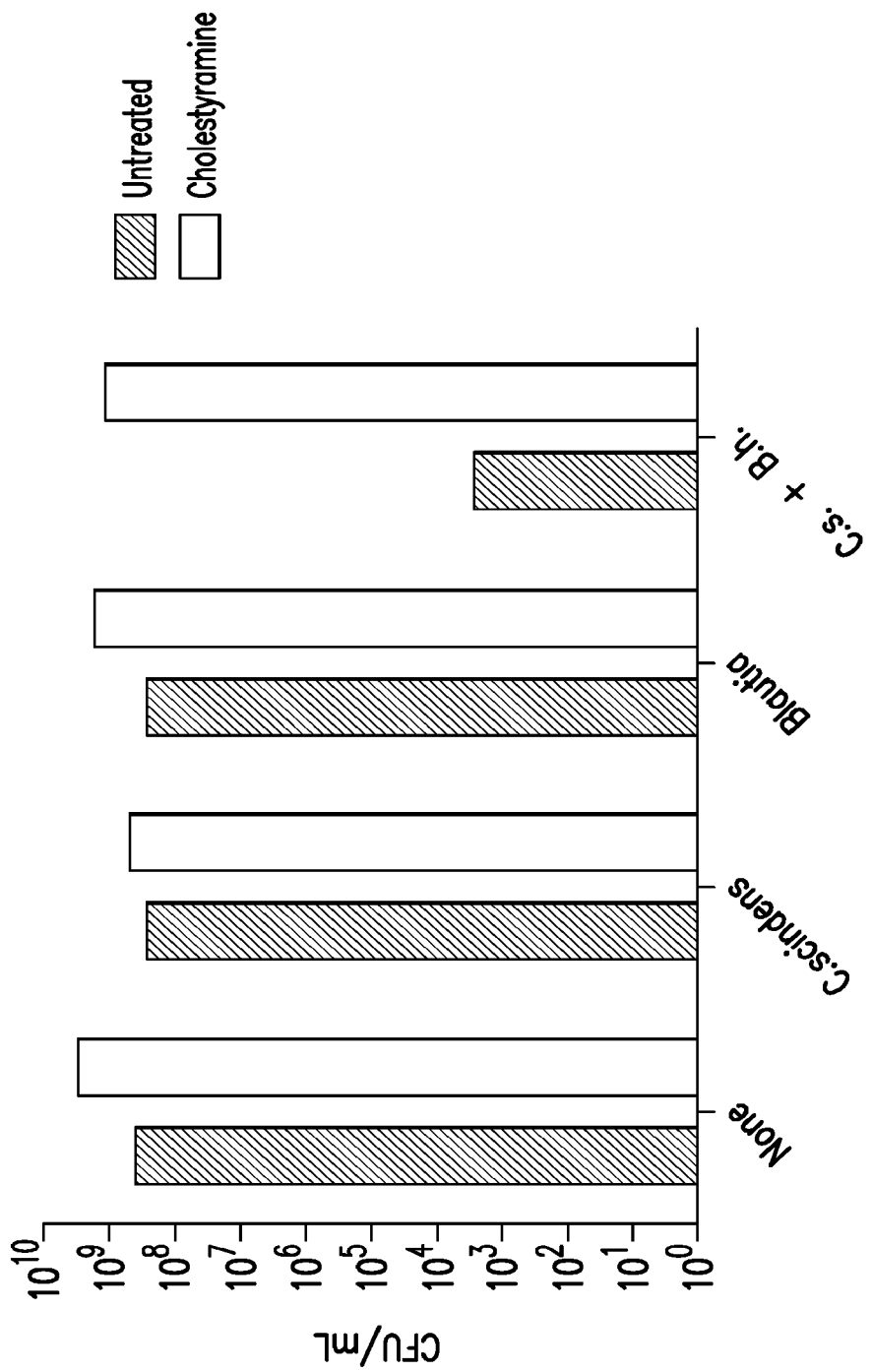

FIG. 3 is a graph of VRE CFU in intestinal extracts infected with VRE and treated with *C. scindens, Blautia*, a mixture of *C. scindens* and *B. hansenii* (C.s.+B.h), or nothing, and also treated with cholesteryamine or untreated.

Figure 4A:
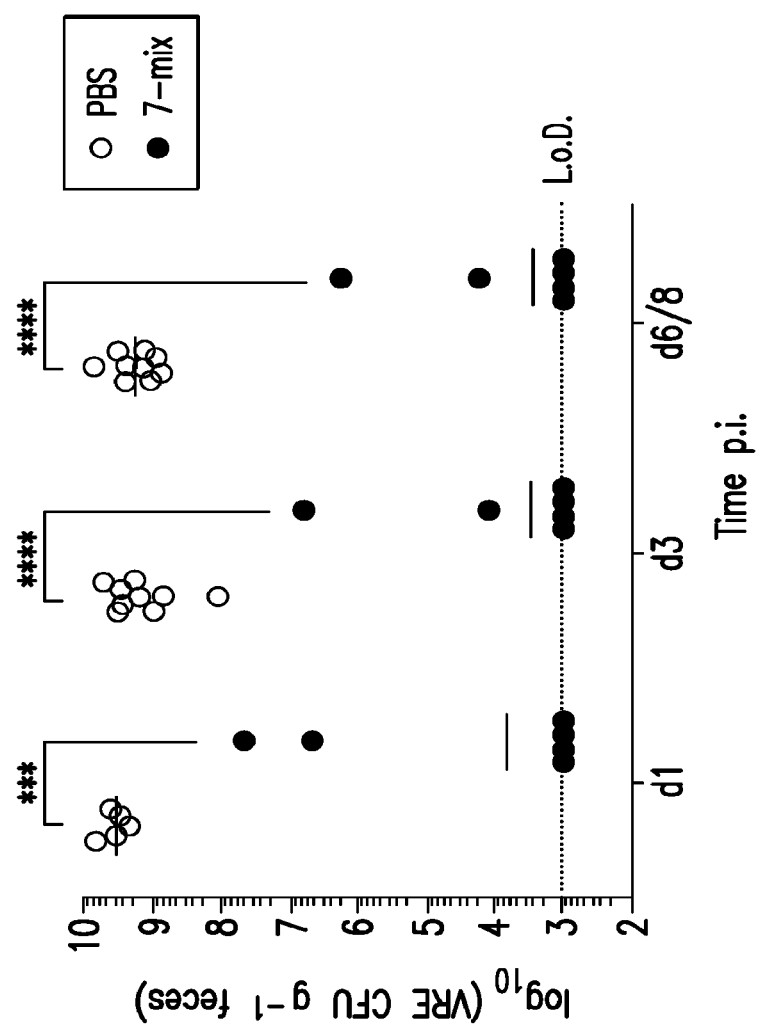
Figure 4B:
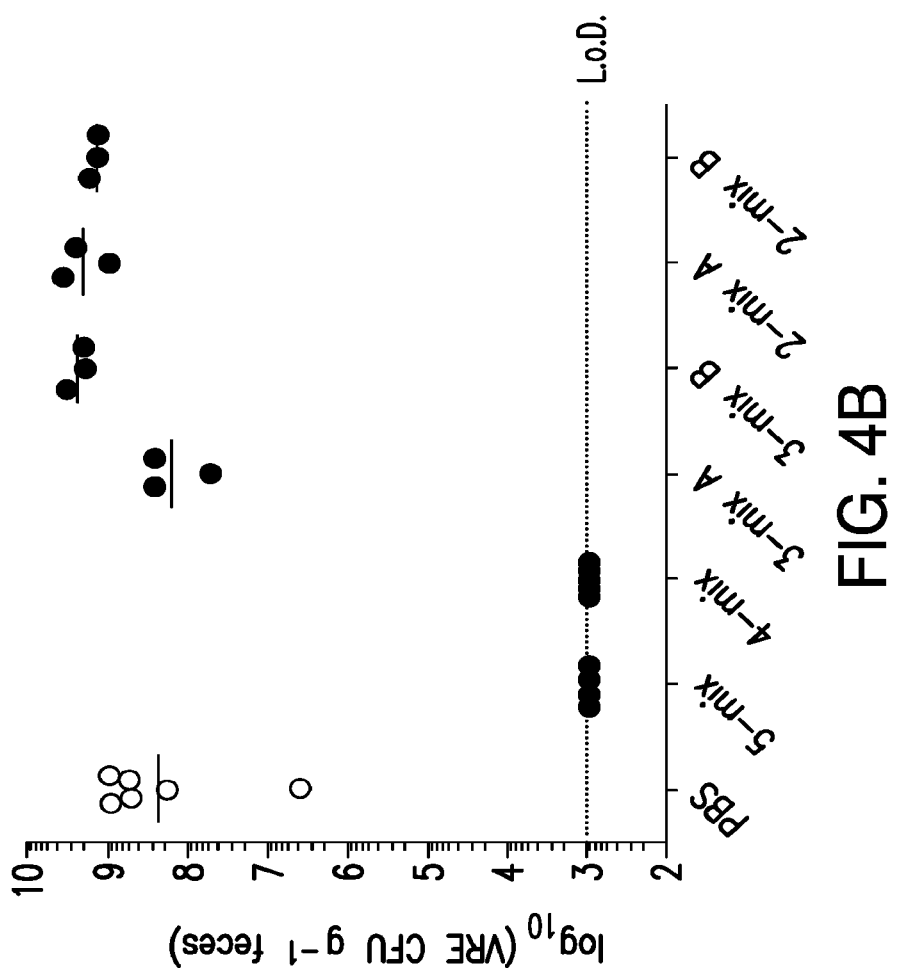

FIGS. 4A-4B show the effect of a bacterial suspension of different mixtures of *A. muciniphila, E. dolichum, B. producta, Blautia* unclassified, *C. bolteae, B. sartorii*, and *P. distasonis* compared to PBS on VRE intestinal clearance in mice in vivo. FIG. 4A is a graph of VRE CFU in mice feces over the study period for a bacterial suspension of all the bacteria (7-mix). FIG. 4B is a graph of VRE CFU in mice feces over the study period for a variety of bacterial suspensions: *A. muciniphila, B. producta, C. bolteae, B.s sartorii*, and *P. distasonis* (5-mix); *B. producta, C. bolteae, B.*

*sartorii*, and *P. distasonis* (4-mix); *C. bolteae, B. sartorii*, and *P. distasonis* (3-mix A); *B. producta, B. sartorii*, and *P. distasonis* (3-mix B); *B. producta* and *C. bolteae*, (2-mix A); and *B. sartorii* and *P. distasonis* (2-mix B).

Figure 5A:
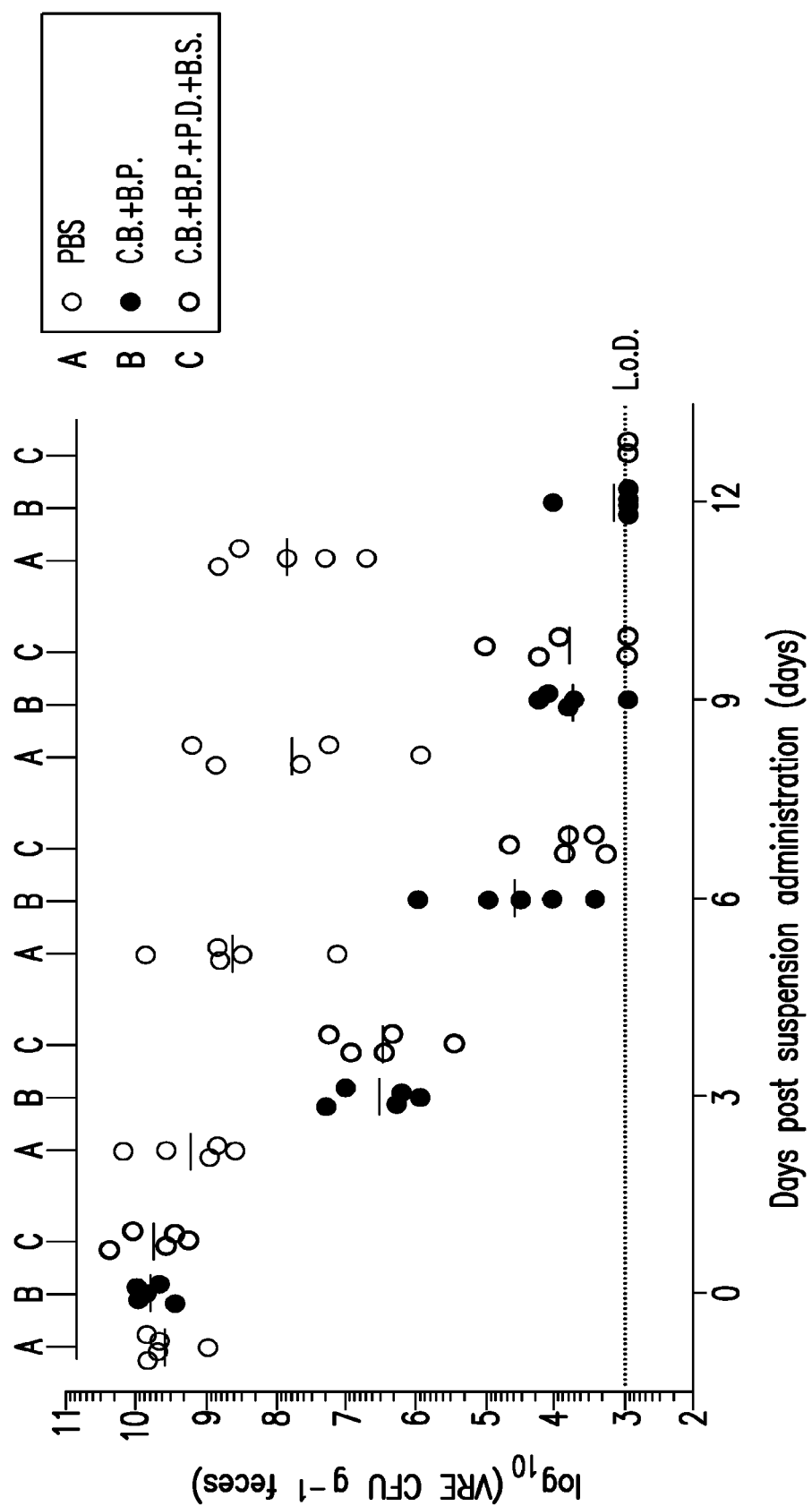
Figure 5B:
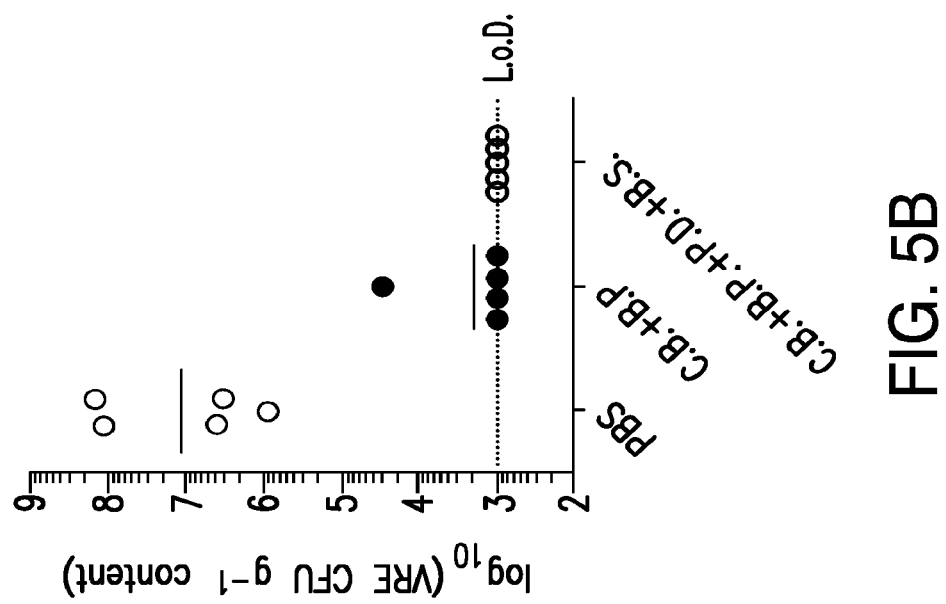

FIGS. 5A-5B show the effects of a mixture of *C. bolteae* and *B. producta* (C.b+B.p), or a mixture of *C. bolteae, B. producta, P. distasonis* and *B. sartorii* (C.b.+B.p+P.d.+B.S) on VRE intestinal clearance in mice in vivo. FIG. 5A is a graph of VRE CFU in mice feces over the study period. FIG. 5B is a graph of VRE CFU in intestinal content at the end of the study period.

Figure 6:
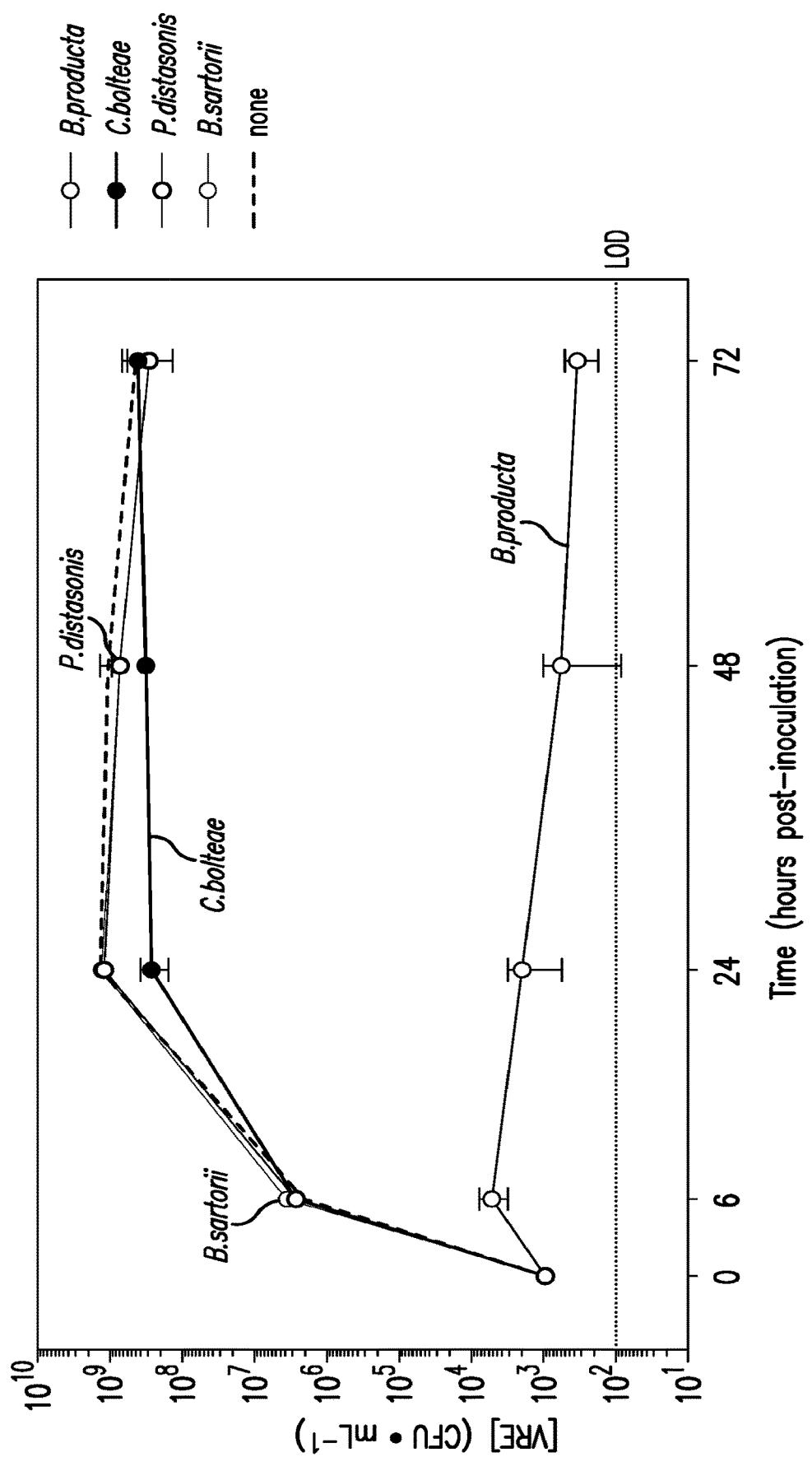

FIG. 6 is a graph of VRE CFU after in vitro co-culture with *C. bolteae, B. producta, B. sartorii*, or *P. distasonis* alone.

5. DETAILED DESCRIPTION OF THE INVENTION

Applicants have discovered bacterial compositions that are capable of increasing resistance to VRE infection or colonization, and/or inhibiting proliferation and/or growth of VRE in a subject.

For clarity of description, and not by way of limitation, this section is divided into the following subsections:
(i) Therapeutic bacteria;
(ii) Recombinant cells;
(iii) Pharmaceutical compositions;
(iv) Methods of treatment; and
(v) Embodiments of the disclosure.

The following are terms relevant to the present invention:

An "individual," "subject," or "patient" herein is a vertebrate, such as a human or non-human animal, for example, a mammal. Mammals include, but are not limited to, humans, non-primates, farm animals, sport animals, rodents and pets. Examples of non-human animal subjects include rodents such as mice, rats, hamsters, and guinea pigs; rabbits; dogs; cats; sheep; pigs; goats; cattle; horses; and non-human primates such as apes and monkeys.

"VRE" as used herein, means vancomycin-resistant *Enterococcus*/i, which in certain embodiments, comprise vancomycin-resistant *E. faecium* and/or vancomycin-resistant *E. faecalis*. If a particular VRE species is intended, such as in certain of the Working Examples, it is specified.

"VRE colonization" or colonization with VRE" as used herein designate colonization of a site in the gastrointestinal tract of a subject with VRE bacteria without a VRE infection symptom or without a VRE infection symptom attributable to VRE colonization. VRE may be detectable by the culture of VRE from or detection of VRE biomarkers in the feces, intestinal contents, sputum, blood, urine, or wound of the subject. VRE biomarkers include VRE-specific nucleic acids or proteins, including protein fragments, and/or nucleic acid or protein profiles, such as VRE-specific 16S rRNA. VRE biomarkers are detectable at least by sequencing, PCR-based tests, and protein assays, and nucleic and/or protein arrays, as applicable for the particular VRE biomarker(s).

"VRE infection" and "infection with VRE" as used herein designate VRE colonization and the presence of one or more VRE infection symptoms. A "VRE infection symptom" includes include one or more symptoms of "Enterocolitis infectious" as defined in the Common Terminology Criteria for Adverse Events, Version 4 (CTCAE), one or more symptoms of "Sepsis" as defined in the CTCAE, and/or one or more of abdominal tenderness, abdominal pain, abdominal cramping, sepsis, endocarditis, meningitis, headache, stiff neck, confusion, back pain, pneumonia, fever, chills, diarrhea, urinary tract infection, endocarditis, elevated white blood cell count, and decreased serum albumin, when such symptom is attributable to VRE colonization.

A "therapeutically effective amount" of a substance as used herein is that amount sufficient to effect beneficial or desired results, including clinical results, and, as such, an "effective amount" depends upon the context in which it is being applied.

In the context of administering a composition to reduce the risk of VRE infection and/or increase resistance to VRE infection in a subject, including reducing such risk and increasing such resistance in a patient colonized with VRE, administering a composition to reduce the severity of VRE infection in a subject, and/or administering a composition to reduce a VRE infection symptom in a subject, an effective amount of a composition described herein is an amount sufficient to treat a VRE infection. In some embodiments, an effective amount can decrease the severity of and/or reduce the likelihood of a VRE infection.

The decrease can be a 10%, 20%, 30%, 40%, 50%, 60%, 70%, 80%, 90%, 95%, 98% or 99% decrease in CFU of VRE in a sample from the subject, such as a gastrointestinal sample, urine, blood, or a wound swab, as compared to an untreated subject with VRE infection. The decrease can be a 10%, 20%, 30%, 40%, 50%, 60%, 70%, 80%, 90%, 95%, 98% or 99% decrease in CFU of VRE in a sample from the subject, such as a gastrointestinal sample, urine, blood, or a wound swab, as compared to the number of CFUs in the subject prior to treatment of the subject.

The decrease can be a 10%, 20%, 30%, 40%, 50%, 60%, 70%, 80%, 90%, 95%, 98% or 99% decrease in severity of VRE infection, as demonstrated by amount of a VRE biomarker in a sample from the subject, such as a gastrointestinal sample, urine, blood, or a wound swab, as compared to an untreated subject with VRE infection. The decrease can be a 10%, 20%, 30%, 40%, 50%, 60%, 70%, 80%, 90%, 95%, 98% or 99% decrease in severity of VRE infection, as demonstrated by amount of a VRE biomarker in a sample from the subject, such as a gastrointestinal sample, urine, blood, or a wound swab, as compared to the severity of infection in the subject prior to treatment.

In some embodiments, the decrease is assayed using a blood biomarker. Such biomarkers can be particularly clinically relevant, as they can strongly correlate with absence or treatment of sepsis resulting from VRE infection.

The decrease can be a 10%, 20%, 30%, 40%, 50%, 60%, 70%, 80%, 90%, 95%, 98% or 99% decrease in progression to VRE infection based on the development of a VRE infection symptom, as compared to an untreated subject with VRE colonization.

An effective amount with respect to VRE infection can be administered in one or more administrations.

In the context of administering a composition to reduce the risk of VRE colonization and/or increase resistance to VRE colonization in a subject, and/or reduce the amount of VRE colonizing the subject, an effective amount of a composition described herein is an amount sufficient to treat VRE colonization. In some embodiments, an effective amount can decrease the severity of and/or reduce the likelihood of a VRE infection.

The decrease can be a 10%, 20%, 30%, 40%, 50%, 60%, 70%, 80%, 90%, 95%, 98% or 99% decrease in CFU of VRE in a sample from the subject, such as a gastrointestinal sample, urine, blood, or a wound swab, as compared to an untreated subject with VRE colonization or an untreated subject without VRE colonization. The decrease can be a 10%, 20%, 30%, 40%, 50%, 60%, 70%, 80%, 90%, 95%, 98% or 99% decrease in CFU of VRE in a sample from the subject, such as a gastrointestinal sample, urine, blood, or a wound swab, as compared to the number of CFUs in the subject prior to treatment of the subject.

The decrease can be a 10%, 20%, 30%, 40%, 50%, 60%, 70%, 80%, 90%, 95%, 98% or 99% decrease in amount of a VRE biomarker in a sample from the subject, such as a gastrointestinal sample, urine, blood, or a wound swab, as compared to an untreated subject with VRE colonization or an untreated subject without VRE colonization. The decrease can be a 10%, 20%, 30%, 40%, 50%, 60%, 70%, 80%, 90%, 95%, 98% or 99% decrease in amount of a VRE biomarker in a sample from the subject, such as a gastrointestinal sample, urine, blood, or a wound swab, as compared to amount of VRE biomarker in the subject prior to treatment.

An effective amount with respect to VRE colonization can be administered in one or more administrations.

As used herein, and as understood in the art, "treatment" or "treating" is an approach for obtaining beneficial or desired results, including clinical results. For purposes of this subject matter, beneficial or desired clinical results include, but are not limited to, prevention, alleviation or amelioration of one or more symptoms, diminishment of extent of disease, stabilized (i.e., not worsening) state of disease, prevention of disease, delay or slowing of disease progression, reduced risk of recurrence of disease, and/or amelioration or palliation of the disease state.

The disease state herein may include VRE infection, and/or one or more VRE infection symptoms. The decrease can be a 10%, 20%, 30%, 40%, 50%, 60%, 70%, 80%, 90%, 95%, 98% or 99% decrease in severity of VRE infection or VRE infection symptoms, such as a decrease in fecal CFU of VRE, a decrease in fecal VRE biomarker, a decrease in blood VRE biomarker, and/or a decrease in urine VRE biomarker as compared to an untreated subject with VRE infection or the same patient prior to treatment. "Treatment" can mean reducing the risk of VRE infection, and/or increasing resistance to VRE infection, and/or reducing the severity of VRE infection in a subject or population. Treatment can also mean a decrease in the grade of a VRE infection as determine by reference to the CTCAE. "Treatment" can also mean a decrease in actual mortality for a patient as compared to a similar patient without treatment or a decrease in the length of time VRE is detectable by fecal CFU, fecal VRE biomarker detection, and/or blood or urine VRE biomarker detection in a patient or patient population as compared to a similar patient or patient population with VRE infection and without treatment.

The disease state herein may also include VRE colonization. The decrease can be a 10%, 20%, 30%, 40%, 50%, 60%, 70%, 80%, 90%, 95%, 98% or 99% decrease in risk of VRE colonization. The decrease may be measured by a decrease in fecal CFU of VRE, a decrease in fecal VRE biomarker, a decrease in blood VRE biomarker, and/or a decrease in urine VRE biomarker as compared to an untreated subject with VRE colonization, an untreated subject without VRE colonization, or the same subject prior to treatment.

For both VRE infection and VRE colonization, treatment can also mean a decrease in the quantity of VRE detectable in a patient or population of patients after treatment as compared to a similar sample from the patient or population of patients prior to treatment, for example a quantitative decrease in the titer of VRE detected in a fecal sample.

The term "expression vector" is used to denote a nucleic acid molecule that is either linear or circular, into which another nucleic acid sequence fragment of appropriate size can be integrated. Such nucleic acid fragment(s) can include additional segments that provide for transcription of a gene encoded by the nucleic acid sequence fragment. The additional segments can include and are not limited to: promoters, transcription terminators, enhancers, internal ribosome entry sites, untranslated regions, polyadenylation signals, selectable markers, origins of replication and such, as known in the art. Expression vectors are often derived from plasmids, cosmids, viral vectors and yeast artificial chromosomes; vectors are often recombinant molecules containing nucleic acid sequences from several sources.

The term "operably linked," when applied to nucleic acid sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

A "regulatory gene" is a gene involved in controlling the expression of one or more other genes.

5.1 Therapeutic Bacteria

In certain embodiments, therapeutic bacteria treat VRE infection or VRE colonization in a subject, and/or reduce the risk of VRE infection or VRE colonization in a subject, and/or increase resistance to VRE infection or VRE colonization in a subject, and/or decrease the severity of VRE infection in a subject, and/or decrease the amount of VRE colonizing a subject.

In certain embodiments, the compositions described herein comprise, consist essentially of, or consist of one or more therapeutic bacteria, or spores thereof, including recombinant therapeutic bacteria, non-recombinant bacteria and bacterial clusters containing therapeutic bacteria.

In certain embodiments, the compositions described herein comprise, consist essentially of, or consist of one or more therapeutic bacteria, or spores thereof, including recombinant therapeutic bacteria, non-recombinant bacteria and bacterial clusters containing therapeutic bacteria in a formulation for administration to a subject.

In certain embodiments, the compositions described herein comprise, consist essentially of, or consist of a mixture of two or more therapeutic bacteria, or spores thereof, including recombinant therapeutic bacteria, non-recombinant bacteria and bacterial clusters containing therapeutic bacteria.

In certain embodiments, the compositions described herein comprise, consist essentially of, or consist of a mixture of two or more therapeutic bacteria, or spores thereof, including recombinant therapeutic bacteria, non-recombinant bacteria and bacterial clusters containing therapeutic bacteria in a formulation for administration to a subject.

In some embodiments, all bacteria in the composition are recombinant. In other embodiments, all bacteria in the composition are non-recombinant. Other compositions include both recombinant and non-recombinant bacteria.

Applicants have discovered that the risk and/or severity of VRE infection can be reduced by increasing conversion of a primary bile salt or acid to a secondary bile salt or acid in a site harboring a VRE, such as the gastrointestinal tract. This is accomplished by introducing to the site harboring a VRE one or more enzymes that wholly or partially covert a primary bile salt or acid to a secondary bile salt or acid, such as one or more enzymes involved in the 7-α/β-dehydroxylation pathway, a nucleic acid encoding such enzymes, such as a nucleic acid including a bile acid-inducible (bai) operon, or a bacterium or mixture of bacteria that can express such enzymes.

In certain embodiments, the therapeutic bacteria increase the conversion of primary bile salts or acids to secondary bile salts or acids when present in a subject. In certain embodiments, one or more native proteins expressed by one or more therapeutic bacteria increase the conversion of primary bile salts or acids to secondary bile salts or acids when present in a subject. In certain embodiments, one or more recombinant proteins expressed in one or more therapeutic bacteria increase the conversion of primary bile salts or acids to secondary bile salts or acids when present in a subject. In certain embodiments, both one or more native proteins expressed by one or more therapeutic bacteria and one or more recombinant proteins expressed in one or more therapeutic bacteria increase the conversion of primary bile salts or acids to secondary bile salts or acids when present in a subject. The one or more native proteins and one or more recombinant proteins may have duplicative and/or complementary functions in conversion of primary bile salts or acids to secondary bile salts or acids when present in a subject.

In certain embodiments, two or more therapeutic bacteria in a mixture of two or more therapeutic bacteria can express proteins that increase the conversion of primary bile salts or acids to secondary bile salts or acids when present in a subject. In certain embodiments, all therapeutic bacteria in a mixture of two or more therapeutic bacteria can express proteins that increase the conversion of primary bile salts or acids to secondary bile salts or acids when present in a subject.

In certain embodiments, one or more therapeutic bacteria in a mixture of two or more therapeutic bacteria may not express proteins that increase the conversion of primary bile salts or acids to secondary bile salts or acids when present in a subject. Such bacteria, which may be referred to as auxiliary therapeutic bacteria, may instead facilitate the survival, growth, and/or protein expression of a protein that treats VRE infection, increases resistance to VRE infection, and/or decreases the severity of VRE infection in a subject, such as a protein that increases the conversion of primary bile salts or acids to secondary bile salts or acids of another therapeutic bacteria. For example, an auxilliary therapeutic bacteria may express beta-lactamase, allowing another therapeutic bacteria that does not express beta-lactamase to survive, grow, and/or express proteins in the presence of an antibiotic. As another example, *C. bolteae* may facilitate the survival, growth, and/or protein expression of *B. producta*.

In certain embodiments, proteins that increase conversion of primary bile acids or salts to secondary bile acids or salts include 20-alpha-hydroxysteroid dehydrogenase, 7-beta-dehydrogenase, 7-alpha-dehydroxylase, and steroid desmolase. In one specific embodiment, the therapeutic bacteria is a *C. scindens*, but alternate or additional bacteria may be comprised in the compositions described herein, for example, bacteria which are naturally occurring or bacteria engineered to express a bai 7-α/β-dehydroxylation operon, or peptides expressed therefrom, such as, for example, an enzyme that converts a primary bile acid to a secondary bile acid, for example, 7-α-hydroxysteroid dehydrogenase. Specific examples of naturally occurring bacteria other than *C. scindens* that may be used to provide said enzyme are *C. hiranonis* and *C. hylemonae* (Ridlon, J. Lipid Res. 53:66-76 (2012), Ridlon, J Lipid Res 47, 241-259 (2006)).

In certain embodiments, proteins expressed by one or more therapeutic bacteria include beta-lactamase, or one or more additional proteins that confer at least one antibiotic resistance in bacteria, such as resistance to an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic.

In certain embodiments, proteins expressed by one or more therapeutic bacteria include proteases or glycosidases, such as a mucinase.

In certain embodiments, the therapeutic bacteria include a *C. scindens* bacterium as described in Morris et al., "*Clostridium scindens* sp. nov., a Human Intestinal Bacterium with Desmolytic Activity on Corticoids," Int J Syst Bacteriol, October 1985, 35:478-481, and/or Krafft et al., "Purification and characterization of a novel form of 20-alpha-hydroxysteroid dehydrogenase from *Clostridium scindens*," J Bacteriol. June 1989, 171:2925-2932. In certain embodiments, *C. scindens* bacteria used in the invention are as deposited in, and available from, the American Type Culture Collection (Manassas, Va.), accession number ATCC 35704, Strain Designation VPI 13733. An exemplary *C. scindens* 16S ribosomal RNA gene sequence is set forth in GenBank Accession No. AF262238, and a *C. scindens* whole genome nucleic acid sequence is set forth in GenBank Accession No. ABFY 02000000. Examples of characteristics of *C. scindens* useful in the present invention are the ability to express at least one of 20-alpha-hydroxysteroid dehydrogenase, 7-beta-dehydrogenase, 7-alpha-dehydroxylase, and steroid desmolase.

In certain embodiments, the therapeutic bacteria include a *B. producta* bacterium as described in Liu et al., "Reclassification of *Clostridium coccoides, Ruminococcus hansenii, Ruminococcus hydrogenotrophicus, Ruminococcus luti, Ruminococcus productus* and *Ruminococcus schinkii* as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces," Int. J. Syst. Evol. Microbiol., 2008, 58:1896-1902 and/or Ezaki et al. "16S ribosomal DNA sequences of anaerobic cocci and proposal of *Ruminococcus hansenii* comb. nov. and *Ruminococcus productus* comb. nov.," Int J Syst Bacteriol. 1994, 44:130-136. In certain embodiments, *B. producta* bacteria used in the invention are as deposited in, and available from, the American Type Culture Collection (Manassas, Va.), accession number ATCC 27340, Strain DSM2950. An exemplary *B. producta* 16S ribosomal RNA gene sequence is set forth in GenBank Accession Nos. D14144 and X94966, and a *B. producta* whole genome nucleic acid sequence is set forth in GenBank Accession No. AUUC00000000.

In certain embodiments, the therapeutic bacteria include both *C. scindens* and *B. producta*.

In certain embodiments, the therapeutic bacteria comprise, consist essentially of, or consist of *C. scindens, B. producta*, or both and one or more members of the Bacteroidetes phylum, such as *B. intestihominis* (see, e.g., Buffie and Pamer, Nature Reviews Immunology 13:790-801), and/or the Firmicutes phylum or Lachnospiraceae family, such as *B. hansenii* (ATCC 27752), and/or *P. capillosus* and/or *C. hiranonis*, and/or *C. hylemonae*, and/or *C. perfringens*, and/or *C. sordellii*, and/or *P. sphenisci*, and/or Lachnospiraceae 5_1_57FAA, Clostridiales VE202-05 and/or Clostridiales VE202-26, optionally in a formulation for administration to a subject.

Additional therapeutic bacteria useful in the invention can be identified as bacteria having at least 95%, e.g., 97%, 98%, 99%, or 100% identity with the full-length 16S rDNA of a bacterium reference herein or with one or more variable regions of a 16S rDNA of a referenced bacterium.

In certain embodiments, the therapeutic bacteria comprise, consist essentially of, or consist of C. scindens and B. hansenii.

In certain embodiments, the therapeutic bacteria comprise, consist essentially of, or consist of B. producta administered in combination with C. bolteae.

In certain embodiments, the therapeutic bacteria comprise, consist essentially of, or consist of one or more of P. distasonis, B. sartorii, B. producta, C. innocuum, A. muciniphila, C. bolteae, Blautia unclassified, E. dolichum, and combinations thereof.

In certain embodiments, the therapeutic bacteria comprise a combination of P. distasonis, B. sartorii, B. producta, C. innocuum, A. muciniphila, C. bolteae, and Blautia unclassified. In certain embodiments, the therapeutic bacteria therapeutic bacteria comprise, consist essentially of, or consist of a combination of A. muciniphila, E. dolichum, B. producta, Blautia unclassified, C. bolteae, B. sartorii, and P. distasonis.

In certain embodiments, the therapeutic bacteria comprise, consist essentially of, or consist of a combination of A. muciniphila, B. producta, C. bolteae, B. sartorii, and P. distasonis.

In certain embodiments, the therapeutic comprise, consist essentially of, or consist of a combination of B. producta, C. bolteae, B. sartorii, and P. distasonis.

In certain embodiments, the therapeutic bacteria comprise, consist essentially of, or consist of a combination of C. bolteae, B. sartorii, and P. distasonis.

In certain embodiments, the therapeutic bacteria comprise, consist essentially of, or consist of a combination of B. producta, B. sartorii, and P. distasonis.

In certain embodiments, the therapeutic bacteria comprise, consist essentially of, or consist of a combination of B. producta, and C. bolteae.

In certain embodiments, the therapeutic bacteria in the composition is in the form of purified bacteria or spores or other progenitors thereof, or alternatively is as a constituent in a mixture of types of bacteria, optionally including one or more probiotic bacteria or probiotic yeast.

In certain embodiments, the present invention provides for pharmaceutical compositions comprising such forms of therapeutic bacterial compositions as described herein, and optionally additional bacteria. The composition is in the form of a liquid, a suspension, a dried (e.g., lyophilized) powder, a tablet, a capsule, a suppository, or an enema fluid, and is administered orally, nasogastrically, or rectally. In certain embodiments, the composition is provided in a food product, for example, a yogurt food product. In certain embodiments, a "food product" means a product or composition that is intended for consumption by a human or a non-human animal. Such food products include any food, feed, snack, food supplement, liquid, beverage, treat, toy (chewable and/or consumable toys), meal substitute or meal replacement.

In certain embodiments, the present invention provides for a composition comprising, consisting essentially of, or consisting of isolated C. scindens bacteria or spores thereof in a formulation suitable for administration to a subject. In specific embodiments, the therapeutic bacteria are in desiccated form and/or comprised in a solid pharmaceutical dosage form such as a capsule or tablet. In other embodiments, the composition further comprising, consisting essentially of, or consisting of a second, third or fourth species of bacteria selected from the group consisting of B. intestihominis, B. hansenii, P. capillosus and combinations thereof, or spores thereof.

In other embodiments, the invention provides for a composition comprising, consisting essentially of, or consisting of one, two, three, four, five, six, seven, eight, nine, or ten or more species of bacteria selected from the group consisting of C. scindens, C. hiranonis, C. hylemonae, C. perfringens, C. sordellii, P. sphenisci, Lachnospiraceae 5_1_57FAA, Clostridiales VE202-05, Clostridiales VE202-26, B. intestihominis, B. hansenii, and P. capillosus, or spores thereof.

In certain embodiments, the present invention provides for a composition comprising, consisting essentially of, or consisting of C. scindens, B. intestihominis, B. hansenii, and P. capillosus bacteria, or spores thereof.

In certain embodiments, the present invention provides for a composition comprising, consisting essentially of, or consisting of C. scindens bacteria or spores thereof and further comprising, consisting essentially of, or consisting of more than two but no more than three of B. intestihominis bacteria, B. hansenii bacteria, or P. capillosus bacteria.

In certain embodiments, the present invention provides for a composition comprising, consisting essentially of, or consisting of up to four species of bacteria, or spores thereof, selected from the group consisting of C. scindens, B. intestihominis, B. hansenii, and P. capillosus bacteria.

In certain embodiments, the present invention provides for a composition comprising, consisting essentially of, or consisting of isolated C. scindens bacteria and isolated B. hansenii bacteria, or spores thereof.

In certain embodiments, the present invention provides for a composition comprising, consisting essentially of, or consisting of one or more species of bacteria, or spores thereof, selected from the group consisting of P. distasonis bacteria, B. sartorii bacteria, B. producta bacteria, C. innocuum bacteria, A. muciniphila bacteria, C. bolteae bacteria, Blautia unclassified bacteria, E. dolichum bacteria, and combinations thereof.

In certain embodiments, the present invention provides for a composition comprising, consisting essentially of, or consisting of P. distasonis bacteria, B. sartorii bacteria, B. producta bacteria, C. innocuum bacteria, A. muciniphila bacteria, C. bolteae bacteria, and Blautia unclassified bacteria, or spores thereof.

In certain embodiments, the present invention provides for a composition comprising, consisting essentially of, or consisting of P. distasonis bacteria, B. sartorii bacteria, B. producta bacteria, A. muciniphila bacteria, C. bolteae bacteria, Blautia unclassified bacteria, and E. dolichum bacteria, or spores thereof.

In certain embodiments, the present invention provides for a composition comprising, consisting essentially of, or consisting of two or more or three or more, but no more than seven or eight, species of bacteria, or spores thereof, selected from the group consisting of P. distasonis bacteria, B. sartorii bacteria, B. producta bacteria, C. innocuum bacteria, A. muciniphila bacteria, C. bolteae bacteria, Blautia unclassified bacteria, E. dolichum bacteria, and combinations thereof.

In one embodiment, the therapeutic bacteria are in a formulation suitable for administration to a subject. In specific embodiments, the therapeutic bacteria are in desiccated form and/or comprised in a solid pharmaceutical dosage form such as a capsule or tablet.

In one embodiment, the composition comprises an excipient.

In various embodiments of the invention, the therapeutic bacteria in the composition are in the vegetative state or as spores, or a mixture thereof.

In certain embodiments, the therapeutic bacteria described herein can be modified, for example, by introducing one or more nucleic acids into the bacteria, thereby producing recombinant bacteria. Such nucleic acids can comprise, for example, a bai 7-α/β-dehydroxylation operon, antibiotic resistance gene, antibiotic susceptibility gene, a protease gene, a glycosidase, and/or a bile salt hydrolase gene, as described herein. Such recombinant bacteria can be prepared as described herein.

In certain embodiments, the composition comprises, consists essentially of, or consists of purified therapeutic bacteria or spores thereof or other progenitors thereof, or therapeutic bacteria or spores there as a constituent in a mixture of types of bacteria, optionally including one or more probiotic bacteria or probiotic yeast, optionally in a formulation for administration to a subject.

"Probiotic bacteria" as used herein include any bacteria that have a beneficial effect to a subject when located in the subject's gastrointestinal system, such as a *Lactobacillus* or a *Bifidobacterium*.

"Probiotic yeast" as used herein include any yeast that can have a beneficial effect to a subject when located in the subject's gastrointestinal system, such as a *Saccharomyces*.

All therapeutic bacteria described herein, whether recombinant or non recombinant, isolated or in a mixture, may be cultured using techniques known in the art, including techniques to produce bacteria or spores thereof or bacterial clusters suitable for administration to a subject.

5.2 Recombinant Cells

The present invention provides for therapeutic compositions that treat VRE infection or VRE colonization in a subject, and/or reduce the risk of VRE infection or VRE colonization in a subject, and/or increase resistance to VRE infection or VRE colonization in a subject, and/or decrease the severity of VRE infection in a subject, and/or decrease the amount of VRE colonizing a subject and that can comprise, for example, small molecule, polypeptide, or nucleic acid molecules, or recombinant cells.

In one embodiment, the composition comprises, consists essentially of, or consists of a recombinant cell expressing an enzyme that converts a primary bile salt or acid to a secondary bile salt or acid. In an example, the recombinant cell includes one or more exogenous nucleic acids encoding said enzyme, wherein the one or more exogenous nucleic acids are operably linked to a promoter, optionally in a formulation for administration to a subject. In certain embodiments, the promoter can be an inducible promoter or a constitutively active promoter. The promoter can be a bai operon promoter, or can be another promoter active in the recombinant cell.

In one embodiment, the composition comprises a recombinant cell that can express a bai 7-α/β-dehydroxylation operon, such as the bai operon in *C. scindens*. In an example, the recombinant cell comprises one or more exogenous nucleic acids encoding a bai 7-α/β-dehydroxylation operon, such as the bai operon in *C. scindens*, wherein the one or more exogenous nucleic acids are operably linked to a promoter.

In certain embodiments, a "bai 7-α/β-dehydroxylation operon" refers to a cluster of genes encoding proteins with enzymatic activity that help convert a primary bile acid to a secondary bile acid. Additional proteins not encoded by the cluster of genes may also play a role in the conversion. For example, the protein can convert a primary bile acid such as cholic acid (CA) and/or chenodeoxycholic acid (CDCA), into a secondary bile acid such as deoxycholic acid (DCA) and lithocholic acid (LCA). In certain embodiments, the protein exhibits dehydroxylation activity. In other embodiments, the protein comprises a 7-α-hydroxysteroid dehydrogenase. Examples of such enzymes are 7α-hydroxysteroid dehydrogenase enzymes expressed by *C. scindens, C. hiranonis, C. hylemonae, C. perfringens, C. sordellii, P. sphenisci,* Lachnospiraceae 5_1_57FAA, Clostridiales VE202-05 and Clostridiales VE202-26, as well as active fragments thereof, and recombinant forms of said enzymes.

In certain embodiments, the 7-α-hydroxysteroid dehydrogenase is a *C. scindens* enzyme having the following amino acid sequence:

1 mrlkdkvilv tastrgigla iaqacakega kvymgarnle rakarademn aaggnvkyvy 61 ndatkeetyv tmieeiieqe gridvlvnnf gssnpkkdlg iantdpevfi ktvninlksv 121 fiasqtavky maengggsii nissvgglip disqiaygts kaainyltkl iavhearhni 181 rcnavlpgmt atdavqdnit ddfrnfflkh tpiqrmglpe eiaaavvyfa sddaayttgq 241 iltvsggfgl atpifgdlse rsdarg (SEQ. ID. No.: 1)
as set forth in GenBank Accession No. AAB61151, which may be encoded by a nucleic acid as set forth in GenBank Accession No. M58473:

(SEQ ID NO: 2)

1 ggccggaatg cagaagttgt ccctggcgtt tttatgaagg cgaccggcat gagatattga 61 acgagacaga ccgggaacag gtatatgaag acctgttcca atggattgaa gatcagaaaa 121 tgacgcagca aaattaggac gctatactta agaaaagtat ccggataatg attacatgaa 181 tatgaaagat atctggaata ctaaaaataa atcatatgga gggattacac atgaggttaa 241 aagacaaagt gattctggtt acagcatcca ccagaggcat tggcctggct atcgctcagg 301 catgtgcgaa agaaggagcc aaagtctaca tgggcgccag gaatctggaa cgcgccaagg 361 cacgggctga cgagatgaat gcggcaggcg gcaatgtaaa gtatgtttac aatgatgcga 421 caaaagaaga gacatacgtg acgatgattg aggaaatcat cgagcaagaa gggcgcatag 481 acgtgcttgt aaataatttc ggctcatcaa atcccaagaa agatcttgga attgccaata

```
-continued
 541 cagacccgga ggtattcatc aagacggtaa atatcaacct aaagagcgta tttatcgcaa 601 gccagacggc tgttaagtat atggcggaaa atggaggtgg aagcatcatc aatatctcat 661 ccgtaggagg cctgatacca gatatctctc agattgccta tggaaccagc aaagcggcaa 721 tcaactatct gacgaaactg atagccgtac acgaggcaag gcataacatc agatgcaatg 781 cggtacttcc aggaatgacg gcaacagatg cggtgcagga taatctgacg gatgacttcc 841 gaaacttctt cttgaagcat acgccaattc agcgtatggg gctcccggaa gagatcgcgg 901 cagccgtagt atacttcgca agcgatgatg ccgcatatac cacaggacag attcttaccg 961 tatctggcgg tttcggactg gcaacgccga tatttggaga tctgtctgaa cgctcagatg 1021 cccgcgggta gaatttcatg ggttaactta atcaaaagca gaatcaggaa aagagacagc 1081 cgggagcggc tgtctctttt atctatagtg cgcctagcgg cgcacgtttc taactttata 1141 ggaaagttct cctttcggag aacttgggga ctaaaatagc ccgctcaaaa gcgggcatag 1201 tgaatcagac ggtttggatt aaaagatgta aaagccctct tcaccaaaat cgtcatcatc 1261 aaggttatca aattcatgta agaaataatc catatccaga agttc.
```

In certain embodiments, said enzyme is provided by a host cell, such as a bacterium, engineered to contain a nucleic acid encoding SEQ ID NO:1 or a protein having one, two, or three conservative substitutions therein, operably linked to a constitutively or inducibly active promoter element, as described herein. In certain embodiments, said enzyme is provided by a host cell, such as a bacterium, engineered to contain and express a nucleic acid comprising SEQ ID NO:2 or a nucleic acid having a sequence that is at least 90 percent, or at least 95 percent, at least 97%, or at least 99 percent homologous thereto (where homology may be determined using standard software such as BLAST or FASTA). In certain embodiments, the enzyme is one of the following, or a combination thereof: an enzyme having the amino acid sequence set forth in GenBank Accession No. EIA17829 (7-α-hydroxysteroid dehydrogenase from C. perfringens); and/or an enzyme having the amino acid sequence as set forth in GenBank Accession No. AAA53556 (7-α-hydroxysteroid dehydrogenase from C. sordellii).

In one embodiment, the recombinant cell further comprises one or more exogenous nucleic acids encoding a bile salt hydrolase, antibiotic resistance gene, an antibiotic susceptibility gene, a protease gene, and/or a glycosidase gene or wherein the nucleic acids are operably linked to a promoter.

In certain embodiments, the bile salt hydrolase is, for example, encoded by a bshA and/or bshb gene of a Lactobacillus acidophilus (See, e.g., McAuliffe et al., Appl Environ Microbiol. 2005 August; 71(8):4925-9). Other examples of bile salt hydrolases are described in Begley et al. (Appl Environ Microbiol. 2006 March; 72(3):1729-38).

Without being bound to any particular theory, a conjugated bile acid is referred to herein as a bile salt. The production of a secondary bile acid from a bile salt involves a two-step process: 1) removal of a conjugated taurine or glycine by a bile salt hydrolase (BSH) enzyme and 2) removal of a hydroxyl group from the steroid ring, for example by enzymes comprising an enzyme encoded by the bai-operon; or oxidation of a hydroxyl group on the steroid ring, for example by a hydroxysterol dehydrogenase enzyme.

In certain embodiments, expression of an antibiotic resistance gene by the recombinant cell reduces the inhibition in growth or survival of the recombinant cell caused by exposure to an antibiotic such as, but not limited to, an antibiotic selected from the group consisting of a beta-lactam antibiotic, clindamycin, a cephalosporin, a quinolone antibiotic, levofloxacin, fluoroquinolone, a macrolide antibiotic, trimethoprim, and a sulfonamide antibiotic, as described herein.

In certain embodiments, expression of an antibiotic susceptibility gene by the recombinant cell increases the inhibition in growth or survival of the recombinant cell caused by exposure to an antibiotic. In certain embodiments, such antibiotics can include, but are not limited to, an antibiotic selected from the group consisting of a beta-lactam antibiotic, clindamycin, a cephalosporin, a quinolone antibiotic, levofloxacin, fluoroquinolone, a macrolide antibiotic, trimethoprim, and a sulfonamide antibiotic, as described herein. In other embodiments, the recombinant cell is susceptible to an antibiotic other than the foregoing antibiotics.

In certain embodiments, expression of a protease or a glycosidase gene by the recombinant cell, such as a mucinase gene, increases degradation of a protein or deglycosylation of a protein in a subject, thereby treating VRE infection in the subject directly or by facilitating survival, growth, or protein production by another therapeutic bacteria.

In certain embodiments, the enzyme that can convert a primary bile acid to a secondary bile acid, for example, 7-α-hydroxysteroid dehydrogenase, can be administered directly to a subject as a therapeutic agent. If enzyme is administered in purified form, it may be administered as a composition in a liquid or solid form, optionally may be lyophilized, optionally may comprise a pharmaceutically suitable solvent and/or carrier.

In certain embodiments, compositions disclosed herein include nucleic acid sequences encoding a bai 7-α/β-dehydroxylation operon, said nucleic acid sequences being part of expression vectors that express the bai 7-α/β-dehydroxylation operon or functional fragments thereof in a suitable host.

In certain embodiments, nucleic acid sequences are optimized for expression of the same proteins or protein fragments in the cell.

In certain embodiments, regulatory sequences sufficient to cause separate expression of distinct proteins or protein fragments in the cell are included in the nucleic acid.

In certain embodiments, such nucleic acid sequences have promoters operably linked to the bai 7-α/β-dehydroxylation operon coding region, said promoter being inducible or constitutive, and, optionally, tissue-specific. In certain embodiments, the promoter comprises a cytomegalovirus (CMV) promoter, or any other promoter known in the art that is effective for expressing a nucleic acid in a eukaryotic cell. For example, tissue-specific promoters as described by Atta, World J Gastroenterol. 2010 Aug. 28; 16(32): 4019-4030. In other embodiments, the promoter comprises a bacterial promoter.

Delivery of nucleic acid into a subject or cell, e.g., bacterial cells of the intestinal microbiota, can be either direct, in which case the subject or cell, e.g., bacterial cells of a subject's intestinal microbiota, is directly exposed to the nucleic acid or nucleic acid-carrying vectors, or indirect, in which case, cells, e.g., a host cell, such as isolated bacterial cells of the intestinal microbiota, are first transformed with the nucleic acids in vitro, then transplanted into the subject. These two approaches are known, respectively, as in situ or ex vivo gene therapy.

For general reviews of the methods of gene therapy, see Kron and Kreppel, CurT Gene Ther 12(5):362-73 (2012); Yi et cit. Curr Gene Ther 11(3):218-28 (2011); Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); Morgan and Anderson, Ann. Rev. Biochem. 62:191-217 (1993); and May, TIBTECH 11(5):155-215 (1993). Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, NY (1990).

In certain examples, the methods of the present invention involve transferring a gene to a host cell in culture by such methods as electroporation, lipofection, calcium phosphate mediated transfection, or viral infection. In general, the method of transfer includes the transfer of a selectable marker to the host cells. The cells are then placed under selection to isolate those host cells that have taken up and are expressing the transferred gene. Those host cells are then delivered to a patient.

In certain embodiments, the nucleic acid can be introduced into cells, e.g., bacterial host cells, prior to administration in vivo of the resulting recombinant cell by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc.

Numerous techniques are known in the art for the introduction of foreign genes into cells (see, e.g., Loeffler and Behr, Meth Enzymol. 217:599-618 (1993); Cohen et al., Meth Enzymol. 217:618-644 (1993); Cline, Pharmac Ther. 29:69-92m (1985)), and can be used in accordance with the present invention, provided that the necessary developmental and physiological functions of the recipient cells are not disrupted.

In one embodiment, the host cell is a *C. scindens*, *Lactobacillus*, *Lactococcus*, such as *Lactococcus lactis*, *Bacillus*, such as *Bacillus subtilis*, *Bifidobacterium*, such as *Bificobacterium bifidum*, or a non-pathogenic *Listeria*, e.g. an attenuated and non-*monocytogenes Listeria*, such as *Listeria innocua*. In one embodiment, a combination of host cells is used.

The resulting recombinant cells can be delivered to a patient by various methods known in the art. The number of cells to be delivered to the patient depends on the desired effect, patient state, etc., and can be determined by one skilled in the art.

In certain embodiments, nucleic acid sequences encoding a bai 7-α/β-dehydroxylation operon are introduced into cells such that they are expressible by the cells or their progeny, and the recombinant cells are then administered in vivo for therapeutic effect. For example, a bacterial progenitor, or stem, or other progenitor cells can be used.

Any stem and/or progenitor cells which can be isolated and maintained in vitro can potentially be used (see e.g. PCT Publication WO 94/08598; Porada and Porada, J. Genet Syndr Gene Ther., May 25; S1. p11:011 (2012); Stemple and Anderson, Cell 71:973-985 (1992); Rheinwald, Meth. Cell Bio. 21A:229 (1980); and Pittelkow and Scott, Mayo Clinic Proc. 61:771 (1986)).

In certain embodiments, the terms "vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below. A "therapeutic vector" as used herein refers to a vector that is acceptable for administration to an animal, and particularly to a human.

A large number of vectors suitable for introducing a heterologous nucleic acid into a cell are known in the art, including plasmid and fungal vectors, which have been described for replication and/or expression in a variety of eukaryotic and prokaryotic hosts. examples include pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

Suitable vectors include, for example, bacteriophages, cosmids, plasmids, naked DNA, DNA lipid complexes, and other recombination vehicles typically used in the art that have been described for expression in a variety of eukaryotic and prokaryotic hosts, and can be used for gene therapy as well as for simple protein expression.

5.3 Pharmaceutical Compositions

In certain embodiments, the present invention provides for pharmaceutical compositions which include a therapeutic composition, as described herein, such as, for example, one or more therapeutic bacteria, including recombinant cells, and/or a bai 7-α/β-dehydroxylation operon, and/or a recombinant cell expressing said bai 7-α/β-dehydroxylation operon, as described herein. Such pharmaceutical compositions can further include at least one other agent, such as a stabilizing compound or additional therapeutic agent, and can be administered in any sterile, biocompatible pharmaceutical carrier, including, but not limited to, saline, buffered saline, dextrose, and water. The pharmaceutical compositions can also further include an excipient. The composition can be in a liquid or lyophilized form and includes a diluent (Tris, citrate, acetate or phosphate buffers) having various pH values and ionic strengths, solubilizer such as Tween® or polysorbate, carriers such as human serum albumin or gelatin, preservatives such as thimerosal, parabens, benzylalconium chloride or benzyl alcohol, antioxidants such as ascorbic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in *Remington's Pharmaceutical Sciences*, 18th ed. A. R. Gennaro, ed. Mack, Easton, Pa. (1980).

In certain embodiments, the methods and compositions of the present invention find use in treating VRE infection or VRE colonization. One or more therapeutic bacteria, including recombinant bacteria, bai 7-α/β-dehydroxylation operon nucleic acids, peptides expressed by a bai 7-α/β-dehydroxylation operon, recombinant cells expressing a bai 7-α/β-dehydroxylation operon, and/or secondary bile acids can be administered to the patient in a pharmaceutically acceptable carrier. The route of administration eventually chosen will depend upon a number of factors and can be ascertained by one skilled in the art.

In certain embodiments, the pharmaceutical compositions of the present invention can be formulated using pharmaceutically acceptable carriers well known in the art in dosages suitable for oral, nasogastric, or rectal administration. Such carriers enable the pharmaceutical compositions to be formulated as tablets, pills, capsules, liquids, gels, syrups, slurries, suspensions, enema formulations, and the like, for oral, rectal or nasogastric administration to a patient to be treated. Formulations can include, for example, polyethylene glycol, cocoa butter, glycerol and the like.

Pharmaceutical compositions suitable for use in the present invention include, in certain embodiments, compositions where the active ingredients are contained in an effective amount to achieve the intended purpose. The amount can vary from one individual to another and will depend upon a number of factors, including the overall physical condition of the patient, e.g., severity of the VRE infection or whether VRE infection or VRE colonization has occurred or whether the composition is being administered prophylactically.

In certain embodiments, the compositions of the present invention can be administered for prophylactic and/or therapeutic treatments. For example, in alternative embodiments, pharmaceutical compositions of the present invention are administered in an amount sufficient to treat VRE infection or VRE colonization. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

Accordingly, in certain embodiments, one ore more therapeutic bacteria, including recombinant bacteria, and/or bai 7-α/β-dehydroxylation operon nucleic acid, peptides expressed by a bai 7-α/β-dehydroxylation operon, recombinant cells expressing a bai 7-α/β-dehydroxylation operon, and/or secondary bile acid can be administered to a patient alone, or in combination with one or more other drugs, nucleotide sequences, lifestyle changes, etc. used in the treatment or prevention of VRE infection or VRE colonization, or symptoms thereof, or in pharmaceutical compositions where it is mixed with excipient(s) or other pharmaceutically acceptable carriers.

Single or multiple administrations of formulations can be given depending on the dosage and frequency as required and tolerated by the patient. In certain embodiments, the formulations should provide a sufficient quantity of active agent to effectively treat the VRE infection or VRE colonization, or symptoms or complications thereof as described herein.

5.4 Methods of Treatment and Use of Therapeutic Bacteria

In certain embodiments, the present invention provides for a method of treating VRE infection or VRE colonization comprising administering, to a subject in need of such treatment, an effective amount of a composition described herein. In certain embodiments, the composition comprises, consists essentially of, or consists of one or more therapeutic bacteria as described herein, including recombinant cells, optionally in a formulation suitable for administration to a subject.

In certain embodiments, the therapeutic bacteria include a *C. scindens* bacterium.

In certain embodiments, the therapeutic bacteria include a *B. producta* bacterium.

In certain embodiments, the therapeutic bacteria include both *C. scindens* and *B. producta*.

In certain embodiments, the therapeutic bacteria comprise, consist essentially of, or consist of *C. scindens*, *B. producta*, or both and one or more members of the Bacteroidetes phylum, such as *B. intestihominis*, and/or the Firmicutes phylum or Lachnospiraceae family, such as *B. hansenii*, and/or *P. capillosus* and/or *Cl. hiranonis*, and/or *C. hylemonae*, and/or *Cl. perfringens*, and/or *C. sordellii*, and/or *P. sphenisci*, and/or Lachnospiraceae 5_1_57FAA, Clostridiales VE202-05 and/or Clostridiales VE202-26.

In certain embodiments, the therapeutic bacteria comprise, consist essentially of, or consist of *C. scindens* and *B. hansenii*.

In certain embodiments, the therapeutic bacteria comprise, consist essentially of, or consist of *B. producta* administered in combination with *C. bolteae*.

In certain embodiments, the therapeutic bacteria the therapeutic bacteria comprise, consist essentially of, or consist of one or more of *P. distasonis*, *B. sartorii*, *B. producta*, *C. innocuum*, *A. muciniphila*, *C. bolteae*, *Blautia* unclassified, *E. dolichum*, and combinations thereof.

In certain embodiments, the therapeutic bacteria comprise a combination of *P. distasonis*, *B. sartorii*, *B. producta*, *C. innocuum*, *Ak. muciniphila*, *C. bolteae*, and *Blautia* unclassified.

In certain embodiments, the therapeutic bacteria therapeutic bacteria comprise, consist essentially of, or consist of a combination of *A. muciniphila*, *E. dolichum*, *B. producta*, *Blautia* unclassified, *C. bolteae*, *B. sartorii*, and *P. distasonis*.

In certain embodiments, the therapeutic bacteria the therapeutic bacteria the therapeutic bacteria comprise, consist essentially of, or consist of a combination of *A. muciniphila*, *B. producta*, *C. bolteae*, *B.s sartorii*, and *P. distasonis*.

In certain embodiments, the therapeutic bacteria the therapeutic bacteria the therapeutic bacteria comprise, consist essentially of, or consist of a combination of *B. producta*, *C. bolteae*, *B. sartorii*, and *P. distasonis*.

In certain embodiments, the therapeutic bacteria the therapeutic bacteria the therapeutic bacteria comprise, consist essentially of, or consist of a combination of *C. bolteae*, *B. sartorii*, and *P. distasonis*

In certain embodiments, the therapeutic bacteria the therapeutic bacteria the therapeutic bacteria comprise, consist essentially of, or consist of a combination of *B. producta, B. sartorii,* and *P. distasonis*

In certain embodiments, the therapeutic bacteria the therapeutic bacteria the therapeutic bacteria comprise, consist essentially of, or consist of a combination of *B. producta,* and *C. bolteae.*

Subjects in need of such treatment or compositions include subjects who are either at risk for developing VRE infection or VRE colonization and/or subjects who have existing VRE infection or VRE colonization.

In certain embodiments, the present invention provides for a method of treating a subject at risk of developing a VRE infection or VRE colonization comprising administering, to the subject, an effective amount of a composition of therapeutic bacteria described herein. In certain embodiments, the compositions comprises, consists essentially of, or consists of one or more therapeutic bacteria as described herein, including recombinant cells, optionally in a formulation suitable for administration to a subject.

Subjects at risk for VRE infection or VRE colonization include individuals who are or have been treated with an antibiotic; individuals who are very young (juvenile) or who are old (geriatric, e.g. humans aged 65 years or older); individuals suffering from an inflammatory bowel disease or condition (including human inflammatory bowel disease IBD, ulcerative colitis or Crohn's Disease); individuals who are hospitalized or in a long-term care facility or who have been, in the past 2, 3, 4, 5, or 6 weeks, hospitalized or in a long-term care facility; individuals with cancer including those undergoing anti-cancer treatment and/or stem cell or bone marrow transplant recipients; individuals who have previously suffered VRE infection or VRE colonization, individuals undergoing immunosuppressive therapy or with an otherwise compromised immune system (e.g. subjects infected with an immunodeficiency causing retrovirus such as HIV, FIV, FLV, etc.) and individuals undergoing solid organ transplantation such as liver transplant.

In certain embodiments, the present invention provides for a method for treating VRE infection or VRE colonization, comprising administering, to a subject in need of such treatment, an effective amount of a composition or therapeutic bacteria described herein, for example, *C. scindens* bacteria.

An effective amount of a composition or therapeutic bacteria described herein is an amount which inhibits proliferation and/or growth of VRE in a subject, including decreasing the amount of VRE colonizing a subject. In some embodiments, inhibiting proliferation means that the number of VRE detected in the subject (e.g., in the subject's feces) is the same or fewer than prior to treatment. In certain embodiments, an effective amount of therapeutic bacteria is at least $10^5$ bacteria, or at least $10^6$ bacteria, or at least $10^7$ bacteria, or at least $10^8$ bacteria, or at least $10^9$ bacteria.

In certain embodiments, the present invention provides for a method for treating VRE infection or VRE colonization, comprising administering, to a subject in need of such treatment, an effective amount of a composition described herein, for example, a recombinant cell or a therapeutic bacteria such as a *C. scindens* bacteria.

Reducing the severity of VRE infection refers to an amelioration in VRE infection symptoms.

In certain embodiments, the present invention provides for a method of treating VRE infection or VRE colonization, comprising administering, to a subject in need of such treatment, an effective amount of an enzyme of *C. scindens* (see Ridlon, J. Lipid Res. 54:2437-2449 (2013)).

In certain embodiments, the present invention provides for a method for treating VRE infection or VRE colonization, comprising administering, to a subject in need of such treatment, an effective amount of an enzyme that converts a bile acid to a secondary bile acid.

In certain embodiments, the present invention provides for a method for treating VRE infection or VRE colonization, comprising administering, to a subject in need of such treatment, an effective amount of a bai 7-α/β-dehydroxylation operon nucleic acid, peptides expressed by a bai 7-α/β-dehydroxylation operon, recombinant cells expressing a bai 7-α/β-dehydroxylation operon, therapeutic bacteria, and/or secondary bile acid. In certain embodiments, the compositions of the present invention are administered in purified form. In certain embodiments, the compositions are contained in and/or produced in the subject by a bacterium or a mixture of bacteria.

In certain embodiments, the present invention provides for a method for treating VRE infection or VRE colonization, comprising administering, to a subject in need of such treatment, an effective amount of a secondary bile acid. Examples of secondary bile acids which may be used include deoxycholic acid, lithocholic acid, or a combination thereof.

In one embodiment, the present invention provides for a method for decreasing the severity of one or more VRE infection symptoms, comprising administering, to a subject in need of such treatment, an effective amount of one or more of a recombinant cell; composition comprising one or more therapeutic bacteria; and an agent selected from the group consisting of an enzyme that converts a bile acid to a secondary bile acid, a secondary bile acid, purified bacteria or spores thereof expressing an enzyme that converts a bile acid to a secondary bile acid, and combinations thereof, as described herein.

A subject treated according to the invention may be concurrently or sequentially treated with one or more agent that reduces the risk of and/or ameliorates VRE infection or VRE colonization, for example, but not limited to, one or more antibiotic for example, but not limited to, metronidazole, and/or fidaxomicin; an immunotherapeutic agent such as an anti-toxin antibody; an herbal remedy such as *Puerariae radix, Scutellariae radix, Rhizoma coptidis,* garlic, or one or more extract thereof; and/or a probiotic bacteria or probiotic yeast including for example, but not limited to, *Lactobaccilus acidophilus, Lactobacillus casei, Bifidobacteriva, Streptococcus thermophilus,* and/or *Saccharomyces boulardii.* In certain embodiments, the treatment does not further comprise administration of cholestyramine. In certain embodiments, the treatment does not further comprise administration of vancomycin.

In certain non-limiting embodiments, the present invention provides the use of any composition described herein, including the use of any therapeutic bacteria and pharmaceutical compositions described herein for treating VRE infection or VRE colonization in a subject. The use may be further characterized by aspects of the methods described above and elsewhere herein.

The present invention also provides for methods of diagnosing or identifying a subject with a VRE infection, or at risk for VRE infection.

In certain embodiments, such methods comprise determining the amount of one more bacteria present in an intestinal microbiota sample of a subject that can convert a primary bile acid to a secondary bile acid, for example, *C.*

*scindens*, wherein the subject is diagnosed or identified as having a VRE infection or VRE colonization, or at risk for VRE infection or VRE colonization, when the amount or amount of the one or more bacteria in the subject's microbiota is lower than a bacteria reference amount. In one embodiment, a bacteria reference amount is a amount of bacteria, for example, *C. scindens* or any other bacteria that can convert a primary bile acid to a secondary bile acid, present in intestinal microbiota, an amount below which is indicative of VRE infection or VRE colonization, or risk of VRE infection or VRE colonization, as determined by a medical doctor or person of skill in the art. In one example, such a reference amount can be the amount of said bacteria in the microbiota of a subject who does not have a VRE infection or VRE colonization, or is not at risk for VRE infection of VRE colonization.

In other embodiments, such methods comprise determining the activity or amount of 7-α-hydroxysteroid dehydrogenase enzyme present in the intestinal microbiota of a subject, wherein the subject is diagnosed or identified as having a VRE infection or VRE colonization, or at risk for VRE infection or VRE colonization, when the activity or amount of 7-α-hydroxysteroid dehydrogenase enzyme in the subject's microbiota is lower than a 7-α-hydroxysteroid dehydrogenase enzyme reference amount. In one embodiment, a 7-α-hydroxysteroid dehydrogenase enzyme reference amount is an activity or amount of 7-α-hydroxysteroid dehydrogenase enzyme present in intestinal microbiota, an amount or activity below which is indicative of VRE infection or VRE colonization, or risk of VRE infection or VRE colonization, as determined by a medical doctor or person of skill in the art. In one example, such a reference amount can be the activity or amount of 7-α-hydroxysteroid dehydrogenase in the microbiota of a subject who does not have a VRE infection or VRE colonization, or is not at risk for VRE infection or VRE colonization.

In other embodiments, such methods comprise quantifying the amount of bai 7-α/β-dehydroxylation operon nucleic acid present in a fecal sample of a subject, wherein the subject is diagnosed or identified as having a VRE infection or VRE colonization, or is at risk for VRE infection or VRE colonization, when the amount of bai 7-α/β-dehydroxylation operon nucleic acid present in the fecal sample is lower than a bai 7-α/β-dehydroxylation operon nucleic acid reference amount. In one embodiment, a bai 7-α/β-dehydroxylation operon nucleic acid reference amount is the amount of bai 7-α/β-dehydroxylation operon nucleic acid present in a fecal sample, an amount below which is indicative of VRE infection or VRE colonization, or risk of VRE infection or VRE colonization, as determined by a medical doctor or person of skill in the art. In one example, such a reference amount can be the amount of bai 7-α/β-dehydroxylation operon nucleic acid present in a fecal sample of a subject who does not have a VRE infection or VRE colonization, or is not at risk for VRE infection or VRE colonization. In certain embodiments, the amount of nucleic acid is quantified using metagenomic sequencing, quantitative PCR, or any other method known in the art for quantifying nucleic acid in a sample.

In certain embodiments, when the amount or activity of the one more bacteria present in an intestinal microbiota sample of a subject that can convert a primary bile acid to a secondary bile acid, the 7-α-hydroxysteroid dehydrogenase enzyme in the subject's microbiota, and/or the amount of bai 7-α/β-dehydroxylation operon nucleic acid present in the fecal sample is above their respective reference amounts, the subject is not administered an antibiotic selected from the group consisting of a bata-lactam antibiotic, clindamycin, a cephalosporin, a quinolone antibiotic, levofloxacin, fluoroquinolone, a macrolide antibiotic, trimethoprim, and a sulfonamide antibiotic.

5.5 Embodiments of the Disclosure

As described herein, the present invention provides for compositions and methods for treating VRE infection or VRE colonization.

In one embodiment, the present invention provides a method for reducing the risk of VRE infection or VRE colonization in a subject, and/or increasing resistance to VRE infection or VRE colonization in a subject, and/or reducing the severity of VRE infection or VRE colonization in a subject, and/or decreasing the amount of VRE colonizing a subject comprising administering, to a subject in need of such treatment, an effective amount of a recombinant cell expressing a bai 7-α/β-dehydroxylation operon, wherein the recombinant cell comprises one or more exogenous nucleic acids encoding a bai 7-α/β-dehydroxylation operon, wherein the one or more exogenous nucleic acids are operably linked to a promoter. In certain embodiments, the recombinant cell further comprises one or more nucleic acids encoding a bile salt hydrolase, antibiotic resistance protein, and/or antibiotic susceptibility protein.

In one example, the one or more exogenous nucleic acids comprises a baiCD gene encoding a 7-α-hydroxysteroid dehydrogenase enzyme.

In certain embodiments, the 7-α-hydroxysteroid dehydrogenase is a bacterial 7-α-hydroxysteroid dehydrogenase, wherein the bacteria is selected from the group consisting of *C. scindens, C. hiranonis, C. hylemonae, C. perfringens, C. sordellii, P. sphenisci*, Lachnospiraceae 5_1_57FAA, Clostridiales VE202-26, Clostridiales VE202-05 and combinations thereof. In certain embodiments, the recombinant cell is a bacterium or spore thereof, for example, a bacterium selected from the group consisting of *C. scindens, Lactobacillus, Lactococcus, Bacillus, Bifidobacterium*, and attenuated and non-*monocytogenes Listeria* strains.

In certain embodiments, the bai 7-α/β-dehydroxylation operon is expressed by the recombinant cell in an amount sufficient to transform a primary bile acid to a secondary bile acid by 7-α/β-dehydroxylation.

In one embodiment, the present invention provides for a method for reducing the risk of VRE infection or VRE colonization in a subject, and/or increasing resistance to VRE infection or VRE colonization in a subject, and/or reducing the severity of VRE infection or VRE colonization in a subject, and/or decreasing the amount of VRE colonizing a subject, comprising administering, to a subject in need of such treatment, an effective amount of a composition comprising two or more isolated bacteria or spores thereof, selected from the group consisting of *C. scindens, B. intestihominis, B. hansenii*, and *P. capillosus*, wherein the two or more isolated bacteria or spores thereof are in a formulation for administration to a subject. In certain embodiments, the composition comprises one or more, two or more, three or more, or four of the foregoing bacteria. In one embodiment, composition comprises *C. scindens* and *Bl. hansenii*.

In one embodiment, the present invention provides for a method for reducing the risk of VRE infection or VRE colonization in a subject, and/or increasing resistance to VRE infection or VRE colonization in a subject, and/or reducing the severity of VRE infection or VRE colonization in a subject, and/or decreasing the amount of VRE colonizing a subject, comprising administering, to a subject in need of such treatment, an effective amount of a composition comprising isolated bacteria or spores thereof, selected from the group consisting of P. distasonis, B. sartorii, B. producta, C. innocuum, A. muciniphila, C. bolteae, Blautia unclassified, E. dolichum, and combinations thereof, wherein the isolated bacteria or spores thereof are in a formulation for administration to a subject.

In one embodiment, the recombinant cell or compositions described herein are formulated for oral or rectal administration, and can optionally further comprise a probiotic bacteria, probiotic yeast, or a combination thereof.

In one example, the formulation for oral or rectal administration is a liquid, suspension, dried powder, tablet, capsule or food product.

The present invention also provides for a method for reducing the risk of VRE infection or VRE colonization in a subject, and/or increasing resistance to VRE infection or VRE colonization in a subject, and/or reducing the severity of VRE infection or VRE colonization in a subject, and/or decreasing the amount of VRE colonizing a subject, comprising administering, to a subject in need thereof, an effective amount of an agent selected from the group consisting of an enzyme that converts a bile acid to a secondary bile acid, a secondary bile acid, purified bacteria or spores thereof expressing an enzyme that converts a bile acid to a secondary bile acid, and combinations thereof.

The present invention also provides for a method for decreasing the severity of a symptom of VRE infection, or one or more conditions associated with VRE infection, comprising administering, to a subject in need of such treatment, an effective amount of one or more of a recombinant cell or composition described herein, and an agent selected from the group consisting of an enzyme that converts a bile acid to a secondary bile acid, a secondary bile acid, purified bacteria or spores thereof expressing an enzyme that converts a bile acid to a secondary bile acid, and combinations thereof, wherein the symptom or condition is selected from the group consisting of fever; abdominal cramping, pain, and/or tenderness; elevated amount of white blood cells in the blood; loss of serum albumin; sepsis; endocarditis; meningitis; headache; stiff neck; confusion; back pain; pneumonia; and combinations thereof.

In one example, the enzyme that converts a bile salt to a secondary bile acid is a 7-α-hydroxysteroid dehydrogenase enzyme.

In another example, the recombinant cell, composition or agent can be administered to the subject in an amount effective to inhibit proliferation of VRE in the subject.

In certain embodiments, the composition administered to a subject comprises purified bacteria or spore thereof selected from the group consisting of C. scindens, C. hiranonis, C. hylemonae, C. perfringens, C. sordellii, P. sphenisci, Lachnospiraceae 5_1_57FAA, Clostridiales VE202-26, Clostridiales VE202-05 and combinations thereof.

In one example, the bacteria is purified C. scindens bacteria.

In other examples, the composition further comprises a second species of bacteria selected from the group consisting of B. intestihominis, B. hansenii, P. capillosus, and combinations thereof.

In other examples, the composition comprises purified C. scindens bacteria and purified B. hansenii bacteria.

In certain embodiments, the composition administered to a subject comprises purified bacteria or spore thereof selected from the group consisting of P. distasonis, B. sartorii, B. producta, C. innocuum, A. muciniphila, C. bolteae, Blautia unclassified, E. dolichum, and combinations thereof.

In other examples, the composition is a secondary bile acid, for example, a secondary bile acid selected from the group consisting of deoxycholic acid, lithocholic acid, and a combination thereof.

In certain embodiments, the methods described herein further comprise administering to the subject, an antibiotic, an immunotherapeutic agent, an herbal remedy, a probiotic, or combinations thereof.

In one embodiment, the methods described herein, further comprise identifying a subject with a VRE infection or VRE colonization, or at risk for VRE infection or VRE colonization, comprising obtaining an intestinal microbiota sample from a subject and determining the amount of one or more bacteria present in the intestinal microbiota sample; comparing the amount of the one or more bacteria in the sample with a reference bacteria amount; and administering the recombinant cell, composition or agent to the subject when the amount of one or more bacteria in the sample is lower than the bacteria reference amount. In certain embodiments, the one or more bacteria is selected from the group consisting of C. scindens, C. hiranonis, C. hylemonae, C. perfringens, C. sordellii, P. sphenisci, Lachnospiraceae 5_1_57FAA, Clostridiales VE202-05, Clostridiales VE202-26, P. distasonis, B. sartorii, B. producta, C. innocuum, A. muciniphila, C. bolteae, Blautia unclassified, E. dolichum, and combinations thereof. In certain embodiments, the method further comprising administering an antibiotic to the subject, wherein, when the amount of the one or more bacteria in the sample is equal to or greater than the bacteria reference amount, the antibiotic administered to the subject is not an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic.

In other embodiments, the methods described herein further comprise identifying a subject with a VRE infection or VRE colonization, or at risk for VRE infection or VRE colonization, comprising obtaining an intestinal microbiota sample from a subject and determining the activity or amount of 7-α-hydroxysteroid dehydrogenase enzyme present in the intestinal microbiota sample; comparing the activity or amount of 7-α-hydroxysteroid dehydrogenase enzyme in the sample with a reference 7α-hydroxysteroid dehydrogenase enzyme activity or amount; and administering the recombinant cell, composition or agent to the subject when the activity or amount of 7-α-hydroxysteroid dehydrogenase enzyme in the sample is lower than the reference 7-α-hydroxysteroid dehydrogenase enzyme activity or amount.

The present invention also provides for a method of diagnosing a subject with a VRE infection or VRE colonization, or at risk for VRE infection or VRE colonization, comprising obtaining an intestinal microbiota sample from a subject and determining the amount of one or more bacteria present in the intestinal microbiota sample; comparing the amount of one or more bacteria in the sample with a reference bacteria amount; and diagnosing the subject as having a VRE infection or VRE colonization, or at risk for VRE infection or VRE colonization, when the amount of the one or more bacteria in the sample is lower than the bacteria reference amount. In certain embodiments, the one or more bacteria is selected from the group consisting of C. scindens, C. hiranonis, C. hylemonae, C. perfringens, C. sordellii, P. sphenisci, Lachnospiraceae 5_1_57FAA, Clostridiales VE202-05, Clostridiales VE202-26, *P. distasonis, B. sartorii, B. producta, C. innocuum, A. muciniphila, C. bolteae, Blautia* unclassified, *E. dolichum* and combinations thereof. In certain embodiments, the method further comprising administering an antibiotic to the subject, wherein, when the amount of the one or more bacteria in the sample is equal to or greater than the bacteria reference amount, the antibiotic administered to the subject is not an antibiotic selected from the group consisting of a 0-lactam antibiotic, clindamycin, a cephalosporin, a quinolone antibiotic, levofloxacin, fluoroquinolone, a macrolide antibiotic, trimethoprim, and a sulfonamide antibiotic.

In other embodiments, the present invention provides for a method of diagnosing a subject with a VRE infection or VRE colonization, or at risk for VRE infection or VRE colonization, comprising obtaining an intestinal microbiota sample from a subject and determining the activity or amount of 7-α-hydroxysteroid dehydrogenase enzyme present in the intestinal microbiota sample; comparing the activity or amount of 7-α-hydroxysteroid dehydrogenase enzyme in the sample with a reference 7-α-hydroxysteroid dehydrogenase enzyme activity or amount; and diagnosing the subject as having a VRE infection or VRE colonization, or at risk for VRE infection or VRE colonization, when the activity or amount of 7-α-hydroxysteroid dehydrogenase enzyme in the sample is lower than the reference 7-α-hydroxysteroid dehydrogenase enzyme activity or amount.

In other embodiments, the methods described herein further comprise identifying a subject with a VRE infection or VRE colonization, or at risk for VRE infection or VRE colonization, comprising obtaining a fecal sample from a subject and quantifying the amount of bai 7-α/β-dehydroxylation operon nucleic acid present in the fecal sample; comparing the amount of bai 7-α/β-dehydroxylation operon nucleic acid in the fecal sample with a reference bai 7-α/β-dehydroxylation operon nucleic acid amount; and administering the recombinant cell, composition or agent to the subject when the amount of bai 7-α/β-dehydroxylation operon nucleic acid in the fecal sample is lower than the reference amount.

In other embodiments, the present invention provides for a method of diagnosing a subject with a VRE infection or VRE colonization, or at risk for VRE infection or VRE colonization, comprising obtaining a fecal sample from a subject and quantifying the amount of bai 7-α/β-dehydroxylation operon nucleic acid present in the fecal sample; comparing the amount of bai 7-α/β-dehydroxylation operon nucleic acid present in the fecal sample with a reference bai 7-α/β-dehydroxylation operon nucleic acid amount; and diagnosing the subject as having a VRE infection or VRE colonization, or at risk for VRE infection or VRE colonization, when the amount of bai 7-α/β-dehydroxylation operon nucleic acid present in the fecal sample is lower than the reference amount.

In certain embodiments, the methods described herein further comprise administering an antibiotic to the subject, wherein, when the amount of one or more bacteria in the sample is equal to or greater than the bacteria reference amount; when the activity or amount of 7-α-hydroxysteroid dehydrogenase enzyme in the sample is greater than the reference 7-α-hydroxysteroid dehydrogenase enzyme activity or amount; or when the amount of bai 7-α/β-dehydroxylation operon nucleic acid present in the fecal sample is greater than the reference amount; wherein the antibiotic administered to the subject is not an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic.

In certain embodiments, the present invention provides for a method of reducing risk of developing a VRE infection symptom in a subject receiving antibiotic therapy, comprising administering, to a subject in need of such treatment, an effective amount of a recombinant cell, composition or agent described herein.

In other embodiments, the present invention provides for a method of preventing or treating VRE infection symptom disease in a subject comprising administering, to a subject in need of such treatment, an effective amount of a recombinant cell, composition or agent described herein. In certain embodiments, the VRE infection symptom is sepsis, endocarditis, meningitis, and/or pneumonia. In certain embodiments, the subject is, has or will receive antibiotic therapy The present invention also provides for a kit comprising the recombinant cell, and/or agent, and/or therapeutic composition described herein.

6. EXAMPLES

The presently disclosed subject matter will be better understood by reference to the following Examples, which are provided as exemplary of the invention, and not by way of limitation. For instance, reference to a particular bacterial strain or strains a "VRE" in these examples and the related figures is made in the context of the experiments described only, and does not imply that only those strains are "VRE" as discussed elsewhere in this specification and claims.

Throughout these examples, VRE CFU per unit weight of feces or other material is used as a measure of colonization of the subject and hence infection by VRE. Although this is not a direct measure of colonization, it is a well-accepted corollary for colonization.

6.1 Example 1: A Mixture of 7 Bacteria Restores Colonization Resistance Against VRE in the Presence of Antibiotics A mixture of seven bacteria, *P. distasonis, B. producta, B. sartorii, C. innoccum, C. bolteae, A. muciniphila*, and an unclassified *Blautia*, were tested for their ability to restore colonization resistance in mice to vancomycin-resistant *E. faecium*. These bacteria were chosen for the intrinsic tendency of certain bacteria in the group to be resistant to ampicillin and the intrinsic ability of other bacteria in the group to synthesize secondary bile acids, or other factors.

Experiments were carried out using 6-8 week-old C57BL/6 female mice purchased from The Jackson Laboratory (Bar Harbor, Me.) and housed in sterile cages with irradiated food and acidified water. 0.5 g/L ampicillin (Fisher Scientific, Hampton, N.H.) was administered to animals in the drinking water and changed every 4 days. Starting 24 hours after antibiotic administration, mice were treated with 3 doses (administered daily) of either PBS or a suspension of 7 bacteria (*P. distasonis, B. producta, B. sartorii, C. innoccum, C. bolteae, A. muciniphila* and an unclassified *Blautia*). grown under anaerobic conditions (7-mix). On the next day following the last 7-mix or PBS dose, mice were dosed with about $5\times10^4$ colony forming units (CFU) of vancomycin-resistant *E. faecium* (VRE). Mice were single-housed at the time of dosing with VRE and treated with ampicillin for the duration of the experiment.

Fecal samples were collected on days 1 and 3 post dosing to monitor VRE colonization. VRE CFU in mice feces were measured.

As shown in FIG. 1 and Table 1, mice treated with the 7-mix bacterial suspension prior to VRE dosing exhibited less VRE growth (as demonstrated by fewer CFU) at both 1 and 3 days after dosing with VRE compared to control mice treated with only PBS prior to dosing with VRE. This demonstrates that the 7-mix bacterial suspension provided colonization resistance against VRE colonization in the presence of antibiotics.

TABLE 1

Effect of 7-mix bacterial suspension on VRE colonization 1 and 3 days after dosing with VRE.

| Treatment | CFUs 1 Day Post-Dosing | CFUs 1 Day Post-Dosing |
|---|---|---|
| PBS | 2.22E+09 | 2.76E+09 |
| PBS | 3.31E+09 | 4.98E+09 |
| PBS | 6.22E+09 | 3.11E+09 |
| PBS | 3.86E+09 | 2.82E+09 |
| PBS | 3.11E+09 | 1.89E+09 |
| PBS | 8.00E+05 | 1.20E+08 |
| PBS | 8.00E+05 | 7.60E+08 |
| PBS | 2.00E+06 | 1.00E+09 |
| 7-mix | 0.00E+00 | 0.00E+00 |
| 7-mix | 4.78E+07 | 1.97E+06 |
| 7-mix | 0.00E+00 | 0.00E+00 |
| 7-mix | 5.04E+06 | 1.75E+04 |
| 7-mix | 0.00E+00 | 0.00E+00 |
| 7-mix | 0.00E+00 | 0.00E+00 |
| 7-mix | 0.00E+00 | 0.00E+00 |
| 7-mix | 0.00E+00 | 0.00E+00 |
| 7-mix | 0.00E+00 | 0.00E+00 |
| 7-mix | 0.00E+00 | 0.00E+00 |

6.2 Example 2: *C. scindens* and *B. hansenii* Reduce VRE Colonization in Mice Intestines In Vivo The present example describes the effect of treating VRE growth with *C. scindens* and *B. hansenii*, two additional secondary bile acid-producing bacteria, in vivo in mice.

C57/B6 mice were treated for 1 week with 0.5 g/L ampicillin in drinking water. On day 7 they were dosed with 5×10$^8$ CFU *E. faecium* ATCC700221 (VRE) by oral gavage. Mice were withdrawn from ampicillin on day 7 and left for 3 additional days to allow the ampicillin to wash out. Mice were then individually housed (Day 0 Post-Reconstitution) and were reconstituted with 3 consecutive daily treatments (Days 0, 1 and 2 post-reconstitution) of PBS (No Treatment), 200 uL of a suspension of a naïve C57/B6 fecal pellet in PBS at a concentration of 10 mg/mL (FMT), 10$^8$ CFU of *C. scindens* ATCC35704 (*C. scindens*), 10$^8$ CFU of *B. hansenii* ATCC27752 (*B. hansenii*), or a 1:1 mix of 10$^8$ CFU *C. scindens* and *B. hansenii* (C.s.+B.h.). 3-4 mice were used per group. VRE burden was determined from fecal pellets on days 0, 7, 15, 24 and 30 post-reconstitution by plating on Enterococcosel medium containing 8 ug/mL vancomycin and 100 ug/mL streptomycin.

A frozen aliquot (~100 mg) of each sample was suspended, while frozen, in a solution containing 500 µl of extraction buffer (200 mM Tris, pH 8.0/200 mM NaCl/20 mM EDTA), 200 µl of 20% SDS, 500 µl of phenol:chloroform:isoamyl alcohol (24:24:1), and 500 µl of 0.1 mm diameter zirconia/silica beads (BioSpec Products). Microbial cells were lysed by mechanical disruption with a bead beater (BioSpec Products) for 2 minutes, after which two rounds of phenol:chloroform:isoamyl alcohol extraction were performed. DNA was precipitated with ethanol and re-suspended in 50 µl of Tris/EDTA (TE) buffer with 100 µg/ml RNase. The isolated DNA was subjected to additional purification with QIAamp Mini Spin Columns (Qiagen).

Amplicons of the V4-V5 16S rRNA region were amplified and sequenced using an Illumina MiSeq platform for samples in the in vivo and ex vivo adoptive transfer experiments. For each sample, duplicate 50-µl PCR reactions were performed, each containing 50 ng of purified DNA, 0.2 mM dNTPs, 1.5 mM MgCl2, 1.25 U Platinum Taq DNA polymerase, 2.5 µl of 10×PCR buffer, and 0.2 µM of each primer designed to amplify the V4-V5: 563F (5'-nnnnnnnn-NNNNNNNNNNNN-AYTGGGYDTAAAGNG-3') (SEQ. ID. NO.: 3) and 926R (5'-nnnnnnnn-NNNNNNNNNNNN-CCGTCAATTYHTTTRAGT-3') (SEQ. ID. NO.: 4). A unique 12-base Golay barcode (Ns) preceded the primers for sample identification, and one to eight additional nucleotides were placed in front of the barcode to offset the sequencing of the primers. Cycling conditions were 94° C. for 3 minutes, followed by 27 cycles of 94° C. for 50 s, 51° C. for 30 s, and 72° C. for 1 minute. A condition of 72° C. for 5 minutes was used for the final elongation step. Replicate PCRs were pooled, and amplicons were purified using the Qiaquick PCR Purification Kit (Qiagen). PCR products were quantified and pooled at equimolar amounts before Illumina barcodes and adaptors were ligated on using the Illumina TruSeq Sample Preparation protocol. The completed library was sequenced on an Illumina Miseq platform following the Ilumina recommended procedures.

Sequences were analyzed using the mothur (version 1.33.3) pipeline. Potentially chimaeric sequences were removed using the UChime algorithm. Sequences with a distance-based similarity of 97% or greater were grouped into OTUs using the average neighbor algorithm and classified using the BLAST (megablast) algorithm and the GenBank 16S rRNA reference database.

As shown in FIG. 2A, treatment of VRE dosed mice with FMT or with *C. scindens* or *B. hansenii* alone reduced VRE burden over the 30-day study. VRE growth was at the lowest detectable limit by day 15 post-reconstitution for FMT and *C. scindens* treated animals. A combination of *C. scindens* and *B. hansenii* did not reduce VRE burden in this example.

However, the amount of VRE spp. 16S sequence reads was decreased by day 15 post-reconstitution for each of the treatment conditions (p~0.1 overall). (See FIG. 2B). Additionally, at day 15 post-reconstitution, mice treated with *C. scindens* alone that cleared VRE had very high amounts of *Blautia* spp. 16S sequence reads (see FIG. 2C), while a single mouse treated with *C. scindens* alone which had not cleared VRE at day 15 had undetectable amounts of *Blautia* spp. 16S sequence reads. Similarly, mice treated with *B. hansenii* alone, or a combination of *C. scindens* and *B. hansenii*, exhibited low amounts of *Blautia* spp. 16S sequence reads at day 15 post-reconstitution. (See FIG. 2C).

These data demonstrate that *B. hansenii* can play a role in reconstitution in the presence of *C. scindens*, but the relationship is complex.

6.3 Example 3: A Combination of *C. scindens* and *B. hansenii* Reduces VRE Growth in Intestinal Extracts Ex Vivo Independent of Bile Acids To further understand their relationship and effects on VRE, *C. scindens* and *Blautia hansenii* were tested for their ability to restore colonization resistance to VRE in mouse intestinal extracts ex vivo.

C57/B6J mice were treated for 3 days with 200 μg of clindamycin by intraperitoneal injection and sacrificed on day 4. Intestinal content was harvested from the small intestine and was transferred to an anaerobic chamber and resuspended in reduced anaerobic PBS to a concentration of 10 mg/mL. Content was then extracted with 50% w/v cholestyramine (a bile acid sequestrant) or nothing for 1 hour with rotation to allow examination of any additional effects of bile acids, which inhibit some bacterial growth. Content was then distributed to 96-well plates and inoculated with $10^4$ CFU of *C. scindens*, *B. hansenii*, a 1:1 mix of *C. scindens* and *B. hansenii*, or an equal amount of PBS. Cultures were then incubated at 37° C. for 6 hours, followed by inoculation with $10^4$ CFU of VRE and overnight incubation at 37° C. in the anaerobic chamber. VRE burden was determined by plating on Enterococcosel agar containing 8 ug/mL vancomycin and 100 ug/mL streptomycin.

As shown in FIG. 3, mouse intestinal extracts treated with cholestyramine, a bile acid binding resin, exhibited greater VRE microbial growth than untreated cultures following VRE inoculation. Addition of a mixture of *C. scindens* and *B. hansenii* to the extracts reduced VRE microbial growth in the untreated extracts following VRE inoculation compared to extracts treated with cholestyramine. These data indicate that, although bile acids affect VRE growth in untreated samples, they have a much greater effect on VRE growth (inhibition) in samples treated with a mixture of *C. scindens* and *B. hansenii*. This indicates that the ability of *C. scindens* and *B. hansenii* to produce secondary bile acids is likely at least partially responsible for their effects in controlling VRE. Accordingly, these data demonstrate that inclusion of these species or species having similar activity, for example, in this assay, are useful for treating and/or preventing VRE infection.

6.4 Example 4: Combinations of *A. muciniphila*, *E. dolichum*, *B. producta*, *Blautia* Unclassified, *C. bolteae*, *B. Sartorii*, and *P. distasonis* Reduce VRE Growth in Intestinal Extracts in Vivo Different combinations of seven bacteria, *A. muciniphila*, *E. dolichum*, *B. producta*, an unclassified *Blautia* species, *C. bolteae*, *B. sartorii*, and *P. distasonis* were tested for their ability to restore colonization resistance to VRE in mouse intestinal extracts in vivo. These bacteria were chosen for the intrinsic ampicillin resistance of some and the intrinsic ability of others to produce secondary bile acids, or other factors.

Experiments were carried out using 6-8 week-old C57BL/6 female mice purchased from The Jackson Laboratory (Bar Harbor, Me.) and housed in sterile cages with irradiated food and acidified water. 0.5 g/L ampicillin (Fisher Scientific, Hampton, N.H.) was administered to animals in the drinking water and changed every 4 days. Starting 24 hours after antibiotic administration, mice were treated with 3 doses (administered daily) of either saline (PBS) or a suspension of bacteria as indicated below that were grown under anaerobic conditions. On the next day following the last bacterial suspension or PBS dose, mice were dosed with about $5\times10^4$ colony forming units (CFU) of vancomycin-resistant *E. faecium* (VRE). Mice were single-housed at the time of dosing with VRE and treated with ampicillin for the duration of the experiment. Fecal samples were collected on days 1, 3 and 6 or 8 post dosing for mice treated with the 7-mixture suspension, and on day 3 post dosing for mice treated with the other mixtures, to monitor VRE colonization. VRE CFU in mice feces were measured.

The bacterial suspensions used are as follows:
7-Mix: *A. muciniphila*, *E. dolichum*, *B. producta*, *Blautia* unclassified, *C. bolteae*, *B. sartorii*, and *P. distasonis*
5-Mix: *A. muciniphila*, *B. producta*, *C. bolteae*, *B. sartorii*, and *P. distasonis*
4-Mix: *B. producta*, *C. bolteae*, *B. sartorii*, and *P. distasonis*
3-Mix A: *C. bolteae*, *B. sartorii*, and *P. distasonis*
3-Mix B: *B. producta*, *B. sartorii*, and *P. distasonis*
2-Mix A: *B. producta*, and *C. bolteae*
2-Mix B: *B. sartorii*, and *P. distasonis*

As shown in FIGS. 4A and 4B, mice treated with the 7-mix bacterial suspension prior to VRE exposure exhibited less VRE growth (as measured by CFU) at days 1, 3 and 6 or 8 after exposure to VRE compared to control mice (treated with PBS prior to exposure to VRE). Mice treated with the 5-mix and 4-mix bacterial suspension prior to VRE exposure also exhibited less VRE growth (as measured by CFU) at day 3 after exposure to VRE compared to control mice (treated with PBS prior to exposure to VRE). *B. sartorii*, and *P. distasonis* are ampicillin-resistant bacteria. In certain embodiments, when antibiotic treatment is continued during and/or after treatment with bacterial mixtures, these two strains are included in the bacterial mixtures.

Overall, the data show that, although mixtures or smaller numbers of bacteria may have some effect, mixtures of multiple bacteria appear to be more effective at controlling VRE growth in vivo. These data also indicate that interactions between the different bacteria are complex.

6.5 Example 5: Combinations of *C. bolteae*, *B. producta*, *B. sartorii*, and *P. distasonis* Reduce VRE Growth in Intestinal Extracts In Vivo Combinations of *C. bolteae*, *B. producta*, *B. sartorii*, and *P. distasonis* were tested for their ability to clear VRE from mouse intestines in vivo.

Experiments were carried out using 6-8 week-old C57BL/6 female mice purchased from The Jackson Laboratory (Bar Harbor, Me.) and housed in sterile cages with irradiated food and acidified water. 0.5 g/L ampicillin (Fisher Scientific, Hampton, N.H.) was administered to animals in the drinking water and changed every 4 days. Mice were treated with ampicillin 7 days prior to dosing about $5\times10^4$ colony forming units (CFU) of vancomycin-resistant *E. faecium* (VRE). Ampicillin treatment was discontinued when the mice were dosed with VRE. The mice were then treated with 3 doses (administered daily) of either saline (PBS) or a suspension of bacteria as indicated below that were grown under anaerobic conditions. Treatment occurred 3, 4 and 5 days after VRE dosing (i.e., days 0, 1 and 2 of the study). Fecal samples were collected on days 0, 3, 6, 9 and 12 post-treatment with the bacterial suspensions to monitor VRE clearance from mouse intestines. Small intestine (ileum) samples were collected on day 12 post-exposure to bacterial mixtures.

The bacterial suspensions used are as follows:
*C. bolteae* and *B. producta* (C.b.+B.p.)
*C. bolteae*, *B. producta*, *B. sartorii*, and *P. distasonis* (C.b.+B.p.+P.d.+B.s)

As shown in FIG. 5A, mice treated with either bacterial suspension after VRE dosing exhibited greater VRE clearance (as measured by CFU) at days 3, 6, 9 and 12 post-treatment with either bacterial suspension compared to control mice (treated with PBS after exposure to VRE). As shown in FIG. 5B, small intestine (ileum) samples also exhibited VRE clearance on day 12 post-exposure to either bacterial suspension. "L.o.D." is the limit of detection.

These data indicate that both bacterial suspensions were effective at clearing VRE, with the mixture also containing *B. sartorii*, and *P. distasonis* being slightly more effective. Accordingly, in some embodiments, a composition useful for treating VRE includes *B. sartorii*, and *P. distasonis* or bacteria having similar features, e.g., ampicillin-resistance.

6.6 Example 4: Effects of *C. bolteae*, *B. producta*, *B. sartorii*, and *P. distasonis* Alone on VRE Growth In Vitro To investigate the effects of *C. bolteae*, *B. producta*, *B. sartorii*, and *P. distasonis* alone on VRE, $10^7$ CFU/ml of the test bacteria, or no bacteria was co-cultured with $10^3$ CFU/mL VRE anaerobically at 37° C. in BHIS liquid medium (Brain Heart Infusion (BHI)+5 g/L yeast extract+1 g/L L-cysteine). Samples were taken and tested for VRE after 6, 24, 48, and 72 hours of co-culture. Results are presented in FIG. 6 and show that *B. producta* alone resulted in substantially less growth of VRE, even after only 6 hours of co-culture. Similar effects were not observed with the other single bacteria, suggesting that bacterial suspensions useful in controlling and clearing VRE may contain *B. producta*. The additional presence of *C. bolteae* further improves results. Accordingly, in some embodiments, a composition comprises *B. producta*. In other embodiments, a composition comprises *B. producta* and *C. bolteae*.

Various references and sequence accession numbers are cited herein, the contents of which are hereby incorporated by reference in their entireties.

---

We claim:

1. A therapeutic composition comprising a Clostridiales VE202-05 bacteria and at least one of a *Clostridium scindens* bacteria, a *Blautia producta* bacteria, or both a *Clostridium scindens* bacteria and a *Blautia producta* bacteria.

2. The therapeutic composition of claim 1, comprising both the *Clostridium scindens* bacteria and the *Blautia producta* bacteria.

3. The therapeutic composition of claim 1, further comprising one or more additional species of bacteria selected from the group consisting of a member of the Bacteroidetes phylum and a member of the Firmicutes phylum.

4. The therapeutic composition of claim 3, wherein the additional species of bacteria that is a member of the Firmicutes phylum is a member of the Lachnospiraceae family.

5. The therapeutic composition of claim 1, further comprising one or more additional species of bacteria selected from the group consisting of a *Barnesiella intestihominis*, *Blautia hansenii*, *Pseudoflavonifractor capillosus*, *Clostridium hiranonis*, *Clostridium hylemonae*, *Clostridium perfringens*, *Clostridium sordellii*, *Proteocatella sphenisci*, Lachnospiraceae 5_1_57FAA, and Clostridiales VE202-26.

6. The therapeutic composition of claim 1, comprising the *Clostridium scindens* bacteria and further comprising a *Blautia hansenii* bacteria.

7. The therapeutic composition of claim 1, comprising the *Blautia producta* bacteria and further comprising a *Clostridium bolteae* bacteria.

8. The therapeutic composition of claim 1, further comprising one or more additional species of bacteria selected from the group consisting of *Parabacteroides distasonis*, *Bacteroides sartorii*, *Clostridium innocuum*, *Akkermansia muciniphila*, *Clostridium bolteae*, *Blautia unclassified*, and *Eubacterium dolichum*.

9. The therapeutic composition of claim 1, further comprising one or more species of bacteria which express an enzyme that can convert a primary bile acid to a secondary bile acid, synthesize an antibiotic resistance molecule, express a protease, or express a glycosidase.

10. The therapeutic composition of claim 1, where one or more of the bacteria are recombinant bacteria which express a recombinant enzyme that can covert a primary bile acid to a secondary bile acid, synthesize a recombinant antibiotic resistance molecule, express a recombinant protease, or express a recombinant glycosidase.

11. The therapeutic composition of claim 10, wherein the recombinant enzyme that can convert a primary bile acid to a secondary bile acid is a bile acid hydroxysterol dehydrogenase enzyme.

12. The therapeutic composition of claim 1, wherein at least one of the bacteria is in the form of a spore.

13. The therapeutic composition of claim 1, which further comprises one or more pharmaceutically acceptable carriers, such that the therapeutic composition is suitable for oral, nasogastric, or rectal administration.

14. The therapeutic composition of claim 13, which further comprises a probiotic bacteria, a probiotic yeast, or a combination thereof.

15. The therapeutic composition of claim 13, which is a liquid, a suspension, a dried powder, a tablet, a capsule, or a food product.

16. The therapeutic composition of claim 1, wherein one or more of the Clostridiales VE202-05 bacteria, the *Clostridium scindens* bacteria, and the *Blautia producta* bacteria, or a combination thereof are lyophilized.

17. The therapeutic composition of claim 5, wherein the one or more additional species of bacteria are lyophilized.

18. The therapeutic composition of claim 8, wherein the one or more additional species of bacteria are lyophilized.

19. The therapeutic composition of claim 9, wherein the enzyme that can convert a primary bile acid to a secondary bile acid is 7-α-hydroxysteroid dehydrogenase.

20. The therapeutic composition of claim 1, wherein at least one of the bacteria is in a vegetative state.

21. The therapeutic composition of claim 3, wherein the one or more additional species of bacteria are lyophilized.

* * * * *